(12) United States Patent
Vilims

(10) Patent No.: US 8,323,277 B2
(45) Date of Patent: Dec. 4, 2012

(54) COMBINATION ELECTRICAL STIMULATING AND INFUSION METHOD

(76) Inventor: Bradley D. Vilims, Evergreen, CO (US)

( * ) Notice: Subject to any disclaimer, the term of this patent is extended or adjusted under 35 U.S.C. 154(b) by 0 days.

(21) Appl. No.: 13/271,312

(22) Filed: Oct. 12, 2011

(65) Prior Publication Data

US 2012/0029420 A1    Feb. 2, 2012

Related U.S. Application Data

(60) Division of application No. 12/033,232, filed on Feb. 19, 2008, now Pat. No. 8,066,702, which is a continuation-in-part of application No. 11/678,516, filed on Feb. 23, 2007, now Pat. No. 7,945,331, which is a continuation-in-part of application No. 11/033,591, filed on Jan. 11, 2005, now Pat. No. 7,386,350.

(51) Int. Cl.
*A61B 18/18* (2006.01)
*A61N 1/18* (2006.01)

(52) U.S. Cl. ............... 606/41; 606/42; 607/117

(58) Field of Classification Search ............... 606/32–45
See application file for complete search history.

(56) References Cited

U.S. PATENT DOCUMENTS

| | | |
|---|---|---|
| 4,612,934 A | 9/1986 | Borkan |
| 5,255,691 A | 10/1993 | Otten |
| 5,342,357 A | 8/1994 | Nardella |
| 5,397,338 A | 3/1995 | Grey et al. |
| 5,423,877 A | 6/1995 | Mackey |
| 5,447,533 A | 9/1995 | Vachon et al. |
| 5,496,360 A | 3/1996 | Hoffmann et al. |
| 5,951,546 A | 9/1999 | Lorentzen |
| 6,002,964 A | 12/1999 | Feler et al. |
| 6,053,916 A | 4/2000 | Moore |
| 6,104,957 A | 8/2000 | Alo et al. |
| 6,136,021 A | 10/2000 | Tockman et al. |
| 6,141,589 A | 10/2000 | Duhaylongsod |
| 6,146,380 A | 11/2000 | Racz et al. |
| 6,148,222 A | 11/2000 | Ramsey |

(Continued)

FOREIGN PATENT DOCUMENTS

WO    WO 81/03272    11/1981

(Continued)

OTHER PUBLICATIONS

"IDET Procedure: IDET (Intradiscal Electrothermal Annuloplasty)", thePAINRELIF.com Website, available at http://www.thepainrelief.com/idet_idet.shtml, printed on Dec. 22, 2004, pp. 1-2.

(Continued)

*Primary Examiner* — Linda C Dvorak
*Assistant Examiner* — Amanda Scott
(74) *Attorney, Agent, or Firm* — Sheridan Ross P.C.

(57) ABSTRACT

A combined electrical and chemical stimulation lead is especially adapted for providing treatment to the spine and nervous system. The stimulation lead includes electrodes that may be selectively positioned along various portions of the stimulation lead in order to precisely direct electrical energy to ablate or electrically stimulate the target tissue. The invention also includes a method of activating electrodes in the electrical stimulation lead whereby an ablative lesion can be formed in a desired shape and size. The invention further includes a method of managing pain in a sacrum of a patient, and a method of assembling an electrical stimulation device.

3 Claims, 27 Drawing Sheets

U.S. PATENT DOCUMENTS

| | | |
|---|---|---|
| 6,161,047 A | 12/2000 | King et al. |
| 6,175,769 B1 | 1/2001 | Errico et al. |
| 6,263,225 B1 | 7/2001 | Howard, III |
| 6,277,112 B1 | 8/2001 | Underwood et al. |
| 6,379,349 B1 | 4/2002 | Muller et al. |
| 6,562,033 B2 | 5/2003 | Shah et al. |
| 6,635,054 B2 | 10/2003 | Fjield et al. |
| 6,656,174 B1 | 12/2003 | Hegde et al. |
| 6,662,055 B1 | 12/2003 | Prutchi |
| 6,735,474 B1 | 5/2004 | Loeb et al. |
| 6,827,716 B2 | 12/2004 | Ryan et al. |
| 6,832,115 B2 | 12/2004 | Borkan |
| 6,845,267 B2 | 1/2005 | Harrison |
| 6,847,849 B2 | 1/2005 | Mamo et al. |
| 6,902,547 B2 | 6/2005 | Aves et al. |
| 6,921,403 B2 | 7/2005 | Cragg et al. |
| 6,936,024 B1 | 8/2005 | Houser |
| 6,971,395 B2 | 12/2005 | Edwards et al. |
| 6,997,941 B2 | 2/2006 | Sharkey et al. |
| 7,014,633 B2 | 3/2006 | Cragg |
| 7,065,412 B2 | 6/2006 | Swoyer et al. |
| 7,069,087 B2 | 6/2006 | Sharkey et al. |
| 7,099,718 B1 | 8/2006 | Thacker et al. |
| 7,169,146 B2 | 1/2007 | Truckai et al. |
| 7,191,018 B2 | 3/2007 | Gielen et al. |
| 7,200,446 B2 | 4/2007 | Borkan |
| 7,241,295 B2 | 7/2007 | Maguire |
| 7,251,529 B2 | 7/2007 | Greenwood-VanMeerveld |
| 7,276,063 B2 | 10/2007 | Davison et al. |
| 7,309,338 B2 | 12/2007 | Cragg |
| 7,369,894 B2 | 5/2008 | Gerber et al. |
| 7,386,350 B2 | 6/2008 | Vilims |
| 7,422,586 B2 | 9/2008 | Morris et al. |
| 7,449,019 B2 | 11/2008 | Uchida et al. |
| 7,462,178 B2 | 12/2008 | Woloszko et al. |
| 7,529,592 B2 | 5/2009 | Cates et al. |
| 7,660,634 B2 | 2/2010 | Vilims |
| 7,771,422 B2 | 8/2010 | Auge et al. |
| 7,797,054 B2 | 9/2010 | Skubitz et al. |
| 7,819,826 B2 | 10/2010 | Diederich et al. |
| 7,819,869 B2 | 10/2010 | Godara et al. |
| 7,824,404 B2 | 11/2010 | Godara et al. |
| 7,945,331 B2 | 5/2011 | Vilims |
| 8,066,702 B2 | 11/2011 | Vilims |
| 2001/0025175 A1 | 9/2001 | Panescu et al. |
| 2003/0195604 A1 | 10/2003 | Ingle et al. |
| 2004/0015202 A1 | 1/2004 | Chandler, III et al. |
| 2004/0243206 A1 | 12/2004 | Tadlock |
| 2005/0096718 A1 | 5/2005 | Gerber et al. |
| 2005/0177209 A1 | 8/2005 | Leung et al. |
| 2005/0177211 A1 | 8/2005 | Leung et al. |
| 2005/0240238 A1 | 10/2005 | Mamo et al. |
| 2005/0277918 A1 | 12/2005 | Shah et al. |
| 2006/0020297 A1 | 1/2006 | Gerber et al. |
| 2006/0106376 A1* | 5/2006 | Godara et al. .......... 606/32 |
| 2006/0155343 A1 | 7/2006 | Vilims |
| 2006/0217705 A1* | 9/2006 | Godara et al. .......... 606/41 |
| 2006/0259026 A1 | 11/2006 | Godara et al. |
| 2007/0156136 A1 | 7/2007 | Godara et al. |
| 2008/0009927 A1 | 1/2008 | Vilims |
| 2009/0099613 A1 | 4/2009 | Vilims |
| 2011/0196361 A1 | 8/2011 | Vilims |

FOREIGN PATENT DOCUMENTS

| | | |
|---|---|---|
| WO | WO 94/02077 | 2/1994 |
| WO | WO 95/10320 | 4/1995 |
| WO | WO 98/19613 | 5/1998 |
| WO | WO 99/43263 | 9/1999 |

OTHER PUBLICATIONS

Intradiscal Electrothermal Therapy; http://www.emedicine.com/neuro/topic707.htm; printed Dec. 22, 2004; 8 pages.

SpineCath Intradiscal Electrothermal Therapy; http://www.spineuniverse.com/displayarticle.php/article217.html; printed Dec. 22, 2004; 3 pages.

An et al.; "Biological Repair of Intervertebral Disc"; SPINE, 2003, vol. 28, No. 15S; pp. S86-S92.

An et al.; "Intradiscal Administration of Osteogenic Protein-1 Increases . . . " SPINE, vol. 30, No. 1, pp. 25-32.

"Pain Management Slnergy System"; Baylis Medical Company Inc., 2006, 2 pages.

Ben-Yishay; News & Highlights—IDET—a new procedure for discogenic back pain; http://www.neurospinewi.com/newsletters/IDET.html; printed Dec. 22, 2004; 3 pages.

De Mattei et al.; "Effects of Pulsed Electromagnetic Fields on Human Articular Chondrocyte Proliferation"; Connect Tissue Res., 2001, vol. 42, No. 4, pp. 269-279.

Freeman, et al., "Does intradiscal electrothermal therapy denervate and repair experimentally induced posterolateral annular tears in an animal model?", Spine, Dec. 1, 2003, vol. 28, No. 23, pp. 2602-2608.

Ganey et al.; "Disc Chondrocyte Transplantation in a Canine Model: A Treatment for Degenerated or Damaged Intervertebral Disc"; SPINE, 2003, vol. 28, No. 23; pp. 2609-2620.

Gruber et al., "Biologic Strategies for the Therapy of Intervertebral Disc Degeneration"; Expert Opinion on Biological Therapy, 2003, vol. 3, No. 8, pp. 1209-1214.

Mathews et al.; "Treatment of mechanical and chemical lumbar discopathy by dextrose 25%"; J Minim Invasive Spinal Tech, vol. 1, Inaugural 2001; pp. 58-61.

O'Neill et al.; "Percutaneous Plasma Decompression Alters Cytokine Expression in Injured Porcine Intervertebral Discs"; Spine J., 2004, vol. 4, No. 1, pp. 88-98.

Walsh et al.; "In Vivo Growth Factor Treatment of Degenerated Intervertebral Discs"; SPINE, vol. 29, No. 2, pp. 156-163.

Wang et al.; "Up-regulation of Chondrocyte Matrix Genes and Products by Electric Fields"; Clinical Ortho. & Related Research; Oct. 2004, 427S: S163-S173.

Yoon et al.; "The Effect of Bone Morphogenetic Protein-2 on Rat Intervertebral Disc Cells in Vitro"; SPINE, vol. 28, No. 16, pp. 1773-1780.

Ahadian, "Pulsed radiofrequency neurotomy: advances in pain medicine," Current Pain and Headache Reports, 2004, vol. 8, pp. 34-40.

Akatov et al., "Percutaneous radiofrequency destruction of the obturator nerve for treatment of pain caused by coxarthrosis," Stereotact Funct Neurosurg, 1997, vol. 69(1-4 Pt 2), pp. 278-280 (Abstract only).

Anis et al., "Use of radio-frequency ablation for the palliative treatment of sacral chordoma," Am. J. Neuronadiol, 2004, vol. 25, pp. 1589-1591.

Atlihan et al., "Anatomy of the Anterior Sacroiliac Joint With Reference to Lumbosacral Nerves," Clinical Orthopaedics and Related Research, 2000, No. 376, pp. 236-241.

Buijs et al., "Radiofrequency treatment of sacroiliac joint-related pain aimed at the first three sacral dorsal rami: a minimal approach," The Pain Clinic, 2004, vol. 16(2), pp. 139-146.

Calvillo et al., "Anatomy and Pathophysiology of the Sacroiliac Joint," Current Review of Pain, 2000, vol. 4, pp. 356-361.

Cohen et al., "Lateral Branch Blocks as a Treatment for Sacroiliac Joint Pain: A Pilot Study," Regional Anesthesia and Pain Medicine, 2003, vol. 28(2), pp. 113-119.

Cohen et al., "Pulsed radiofrequency as a treatment for groin pain and orchialgia," Urology, 2003, vol. 61(3), pp. 645xxi-xxiii.

Cohen, "Sacroiliac Joint Pain: A Comprehensive Review of Anatomy, Diagnosis, and Treatment," Anesthesia & Analgesia, 2005, vol. 101(5), pp. 1440-1453.

Cole et al., "The Sacroiliac Joint: A Functional Approach," Critical Reviews in Physical and Rehabilitation Medicine, 1996, vol. 8(1&2), pp. 125-152.

Conaghan et al., "Sacral nerve stimulation can be successful in patients with ultrasound evidence of external anal sphincter disruption," Diseases of the Colon and Rectum, 2005, vol. 48(8), pp. 1610-1614.

Davies et al., "Radiofrequency Treatment in the United States," Pain Practice, 2002, vol. 2(3), pp. 192-194.

Deer, "Chapter 6: Injections for the Diagnosis and Treatment of Spinal Pain," American Society of Anesthesiologists, Inc., 2004, vol. 32, pp. 53-69.

Dreyfuss et al., "Chapter 32: Radiofrequency Neurotomy of the Zygapophyseal and Sacroiliac Joints," Pain Procedures, 2000, pp. 395-420.

Ebraheim et al., "Anatomic Considerations for Posterior Approach to the Sacroiliac Joint," Spine, 1996, vol. 21(23), pp. 2709-2712.
Ferrante et al., "Radiofrequency sacroiliac joint denervation for sacroiliac syndrome," Regional Anesthesia and Pain Medicine, 2001, vol. 26(2), pp. 137-142.
Fortin et al., "Three Pathways between the Sacroiliac Joint and Neural Structures," Am. J. Neruoradiol., 1999, vol. 20, pp. 1429-1434.
Fortin et al., "Sacroiliac Joint Innervation and Pain," The American Journal of Orthopedics, 1999, pp. 687-690.
Fukui et al., "Successful relief of hip joint pain by percutaneous radiofrequency nerve thermocoagulation in a patient with contraindications for hip arthroplasty," Journal of Anesthesia, 2001, vol. 15, pp. 173-175.
Gevargez et al., "CT-guided percutaneous radiofrequency denervation of the sacroiliac joint," Eur Radiol., 2002, vol. 12, pp. 1360-1365.
Gopalani et al., "A novel technique for treating nonsurgical hip pain with radiofrequency lesioning of the sensory branches of the obturator and femoral nerves: a case report," Archives of Physical Medicine and Rehabilitation, Poster 102, 2003, vol. 84, A23.
Jiang et al., "Comparison between radiofrequency coagulation plus small needle knife and single method in treatment of sacrolumbar pain," Chinese Journal of Clinical Rehabilitation, 2003, vol. 7(20), pp. 2844-2845 (Abstract only).
Kawaguchi et al., "Percutaneous radiofrequency lesioning of sensory branches of the obturator and femoral nerves for the treatment of hip joint pain," Regional Anesthesia and Pain Medicine, 2001, vol. 26(6), pp. 576-581.
Kirkham et al., "Neuromodulation through sacral nerve roots 2 to 4 with a Finetech-Brindley sacral posterior and anterior root stimulator," Spinal Cord, 2002, vol. 40(6), pp. 272-281.
Kirsch et al., "Proton radiotherapy for Hodgkin's disease in the sacrum," Lancet Oncology, 2005, vol. 6, pp. 532-533.
Kline et al., "Chapter 19: Radiofrequency techniques in clinical practice," Interventional Pain Management, 2001, pp. 243-290 (2001).
Leng et al., "How sacral nerve stimulation neuromodulation works," Urol. Clin. North. Am., 2005, vol. 32(1), pp. 11-8 (Abstract only).
Liguoro et al., "The Posterior Sacral Foramina: An Anatomical Study," 1999, J. Anat., vol. 195, pp. 301-304.
Murata et al., "Origin and pathway of sensory nerve fibers to the ventral and dorsal sides of the sacroiliac joint in rats," Journal of Orthopaedic Research, 2001, vol. 19, pp. 379-383.

Plancarte et al., "Radiofrequency Procedures for Sacral and Pelvic Region Pain," Pain Practice, 2002, vol. 2(3), pp. 248-249.
Pino et al., "Morphologic analysis of bipolar radiofrequency lesions: implications for treatment of the sacroiliac joint," Regional Anesthesia and Pain Medicine, 2005, vol. 30(4), pp. 335-338.
Raj et al., "Executive Summary: The Current Status of the Practice of Radiofrequency in the World," Pain Practice, 2002, vol. 2(3), pp. 176-179.
Simon, "Chapter 50: Sacroiliac joint injection and low back pain," Interventional Pain Management, 2001, pp. 535-539.
Slipman et al., "Sacroiliac Joint Syndrome," Pain Physician, 2001, vol. 4(2), pp. 143-152.
Valleylab-RF Pain Management System, Sep. 16, 2004, available at internet archives, http://www.valleylab.com/static/pain/products-generator.html, 2 pages.
Van Zundert et al. "Application of Radiofrequency Treatment in Practical Pain Management: State of the art," Pain Practice, 2002, vol. 2(3), pp. 269-278.
Yin et al., "Sensory stimulation-guided sacroiliac joint radiofrequency neurotomy: technique based on neuroanatomy of the dorsal sacral plexus," Spine, 2003, vol. 28(20), pp. 2419-2425.
International Search Report for International (PCT) Patent Application No. PCT/US06/00312, mailed Jul. 19, 2006.
Written Opinion for International (PCT) Patent Application No. PCT/US06/00312, mailed Jul. 19, 2006.
International Preliminary Report on Patentability for International (PCT) Patent Application No. PCT/US06/00312, issued Jul. 17, 2007.
Supplementary European Search Report for European Patent Application No. 06717501, mailed Mar. 31, 2008.
Supplementary European Search Report for European Patent Application No. 06717501, mailed Aug. 20, 2008.
Partial European Search Report for European Patent Application No. 08101856.6, mailed Jul. 3, 2008.
Partial European Search Report for European Patent Application No. 08101856.6, mailed Oct. 28, 2008.
Partial European Search Report for European Patent Application No. 08151981.1, mailed Jul. 16, 2008.
Extended European Search Report for European Patent Application No. 08151981.1, dated Dec. 9, 2008.

* cited by examiner

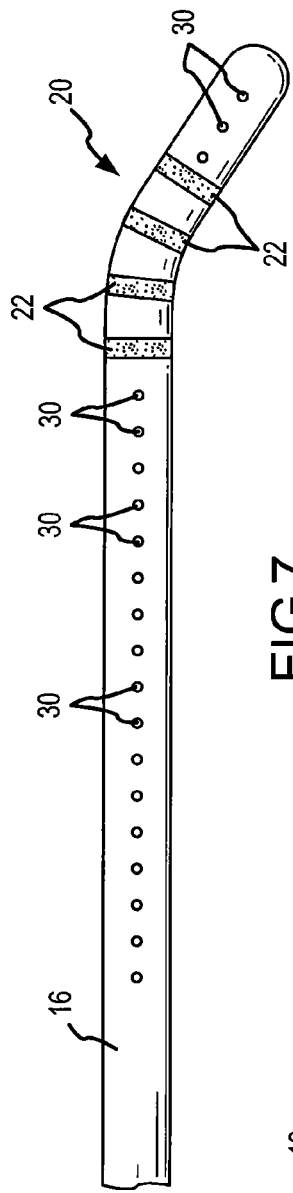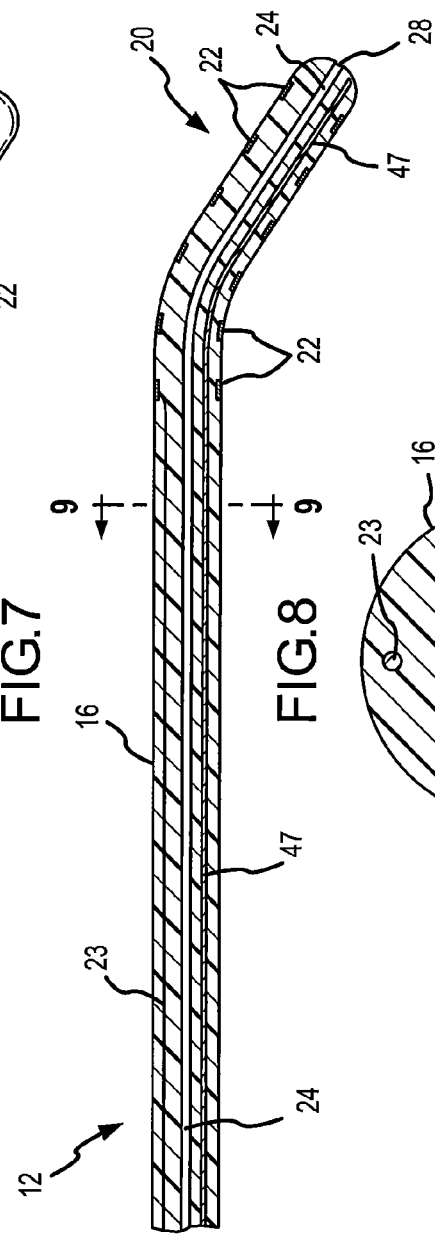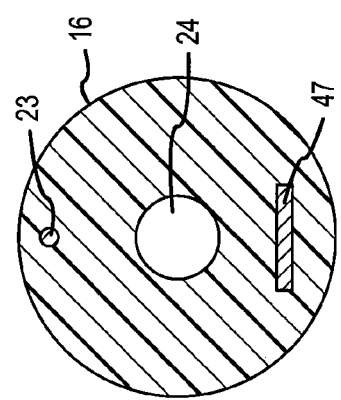

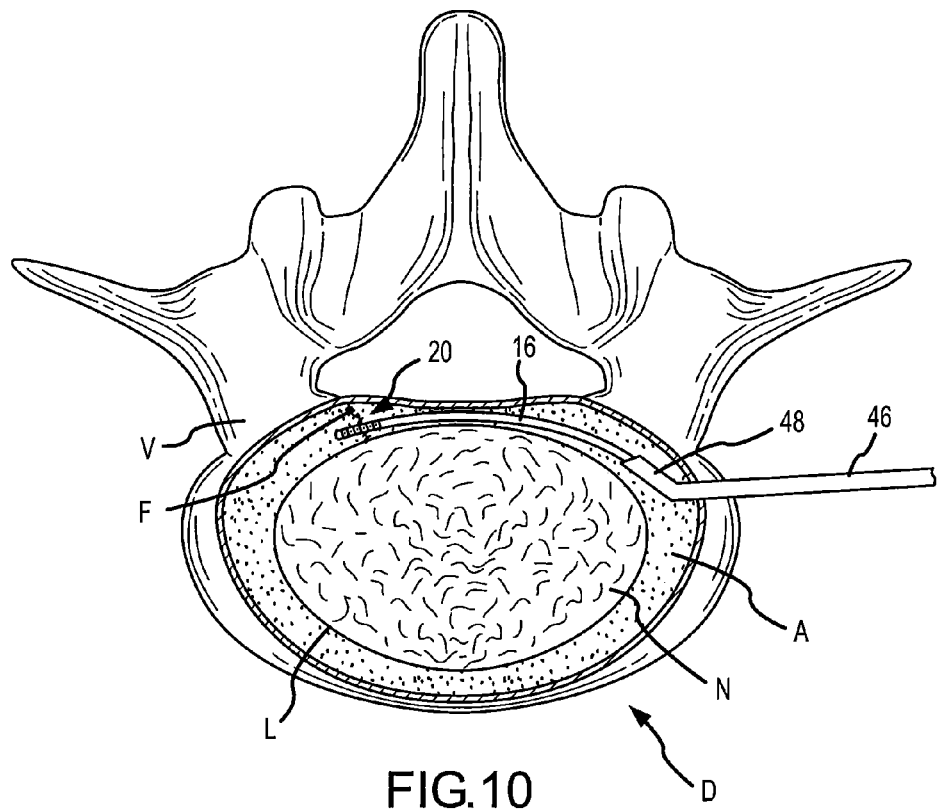
FIG. 10
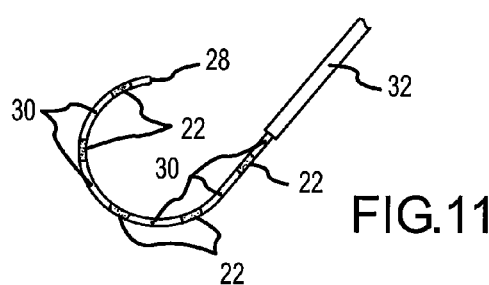
FIG. 11
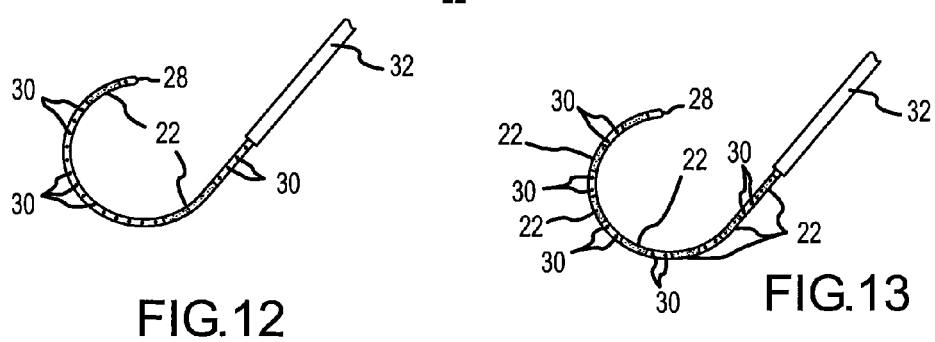
FIG. 12
FIG. 13

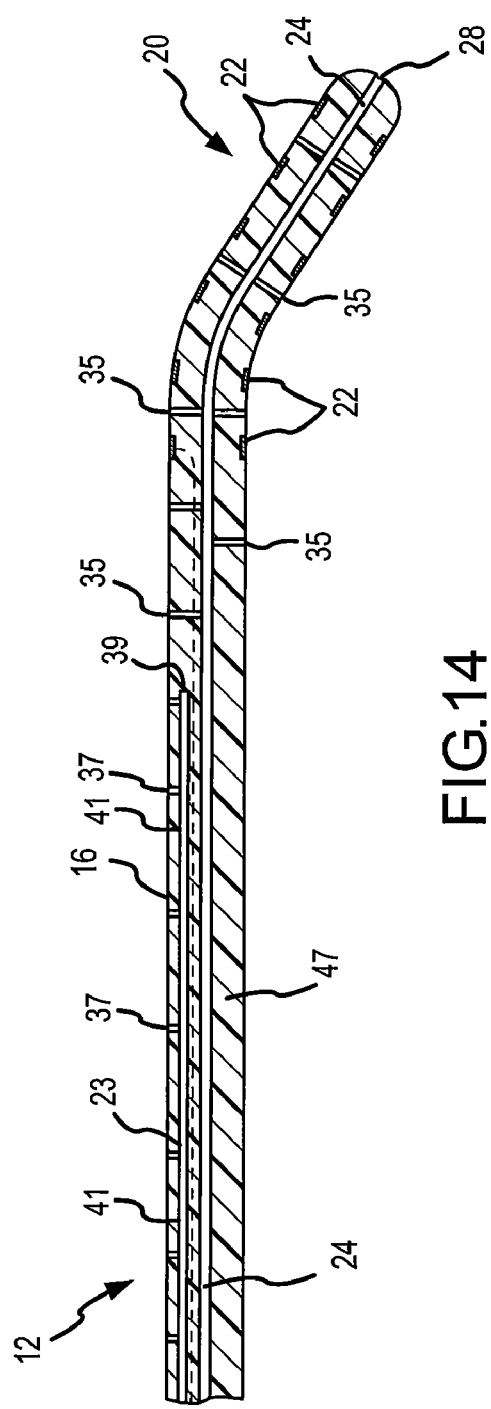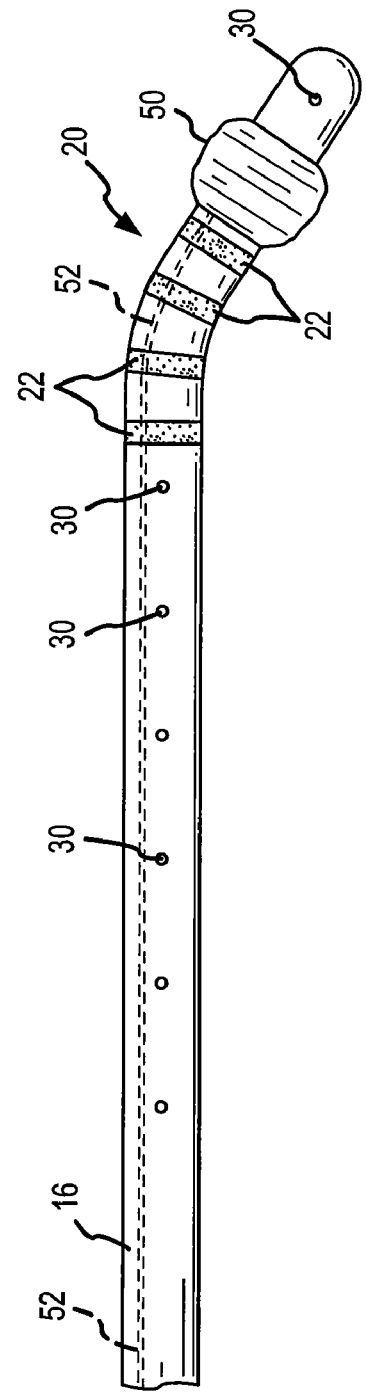
FIG. 14
FIG. 15

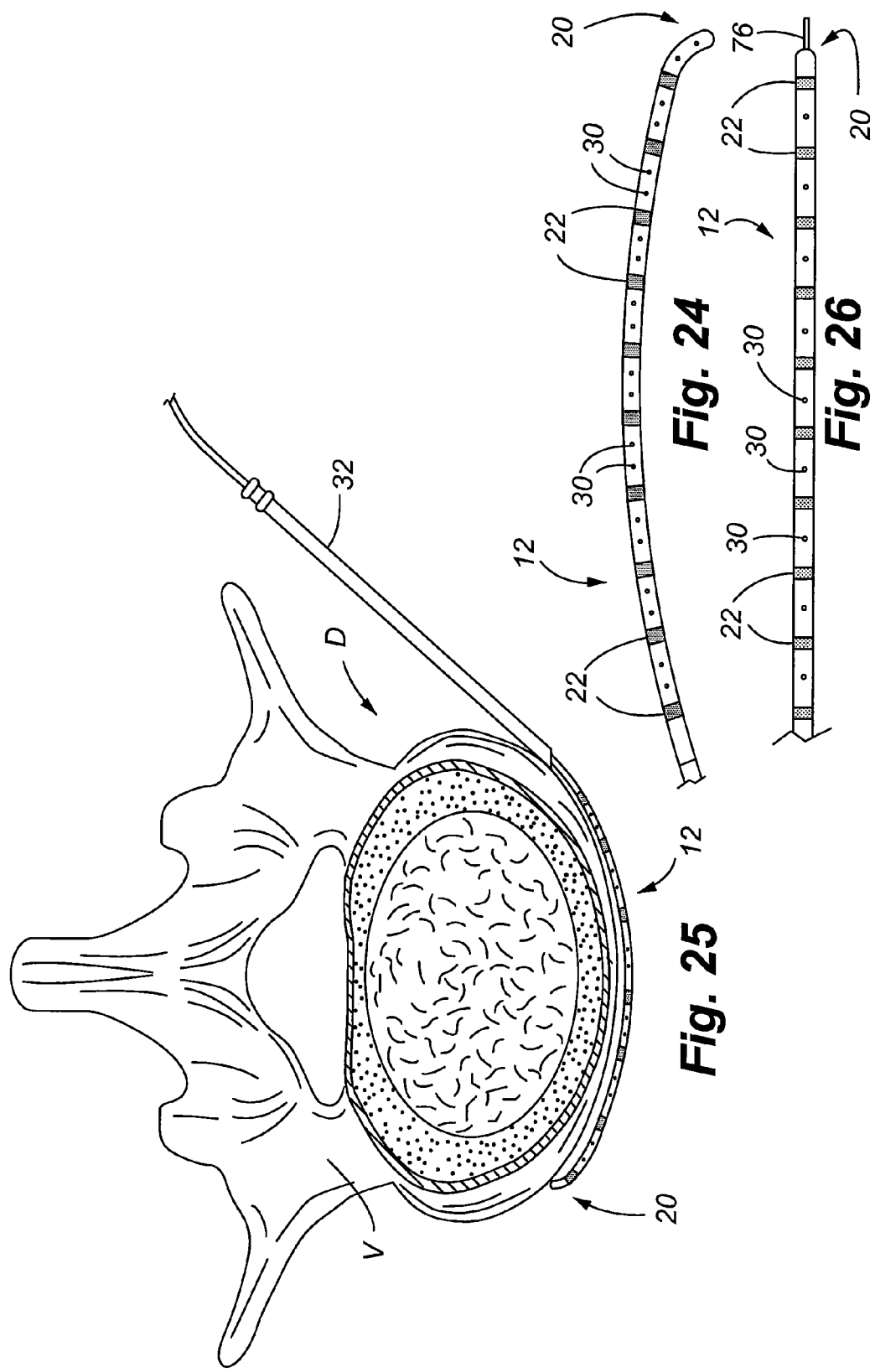

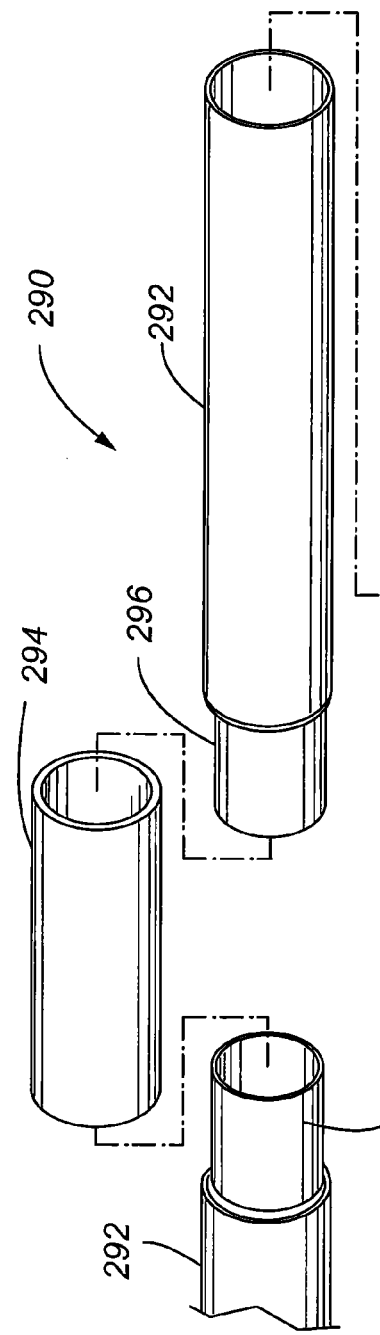
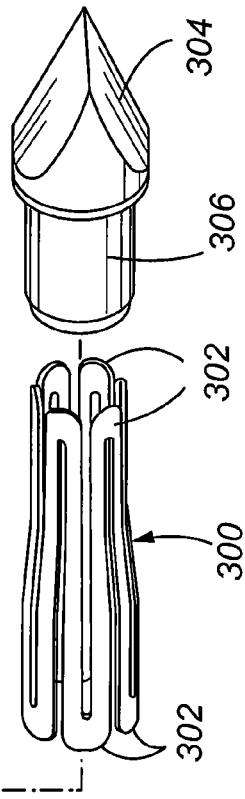
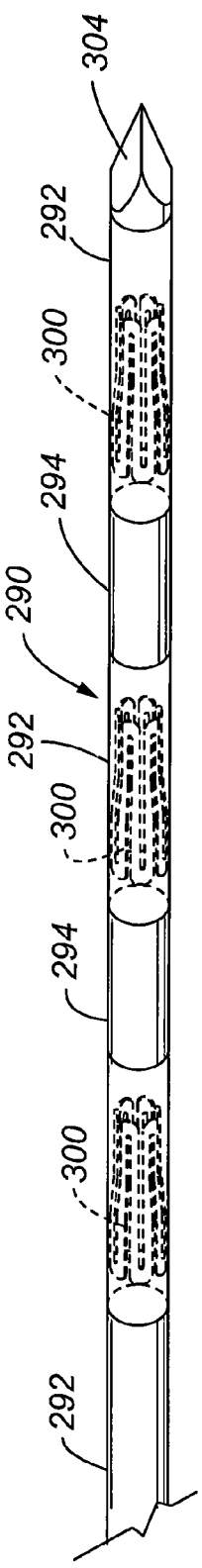
Fig. 29
Fig. 30

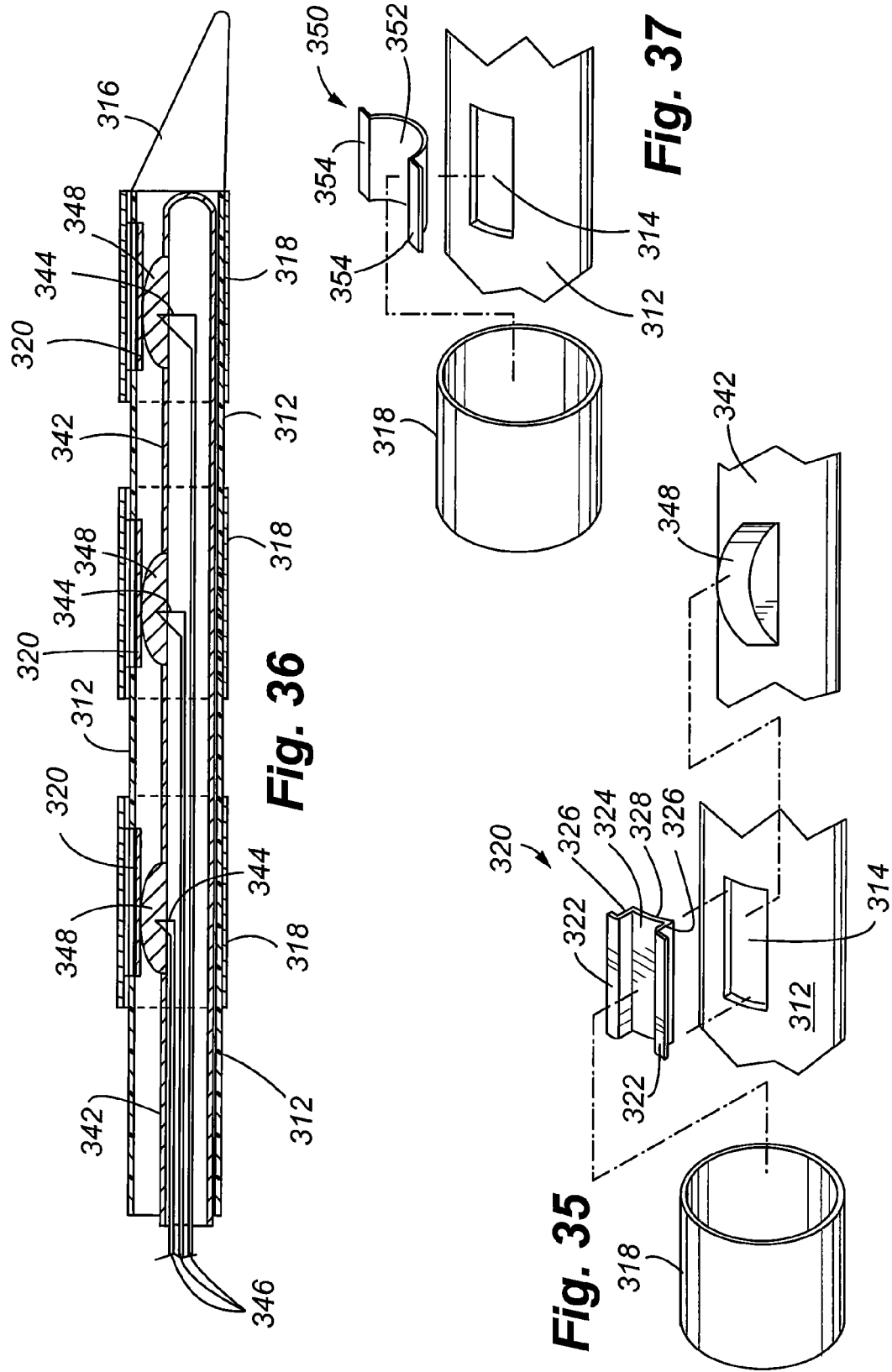

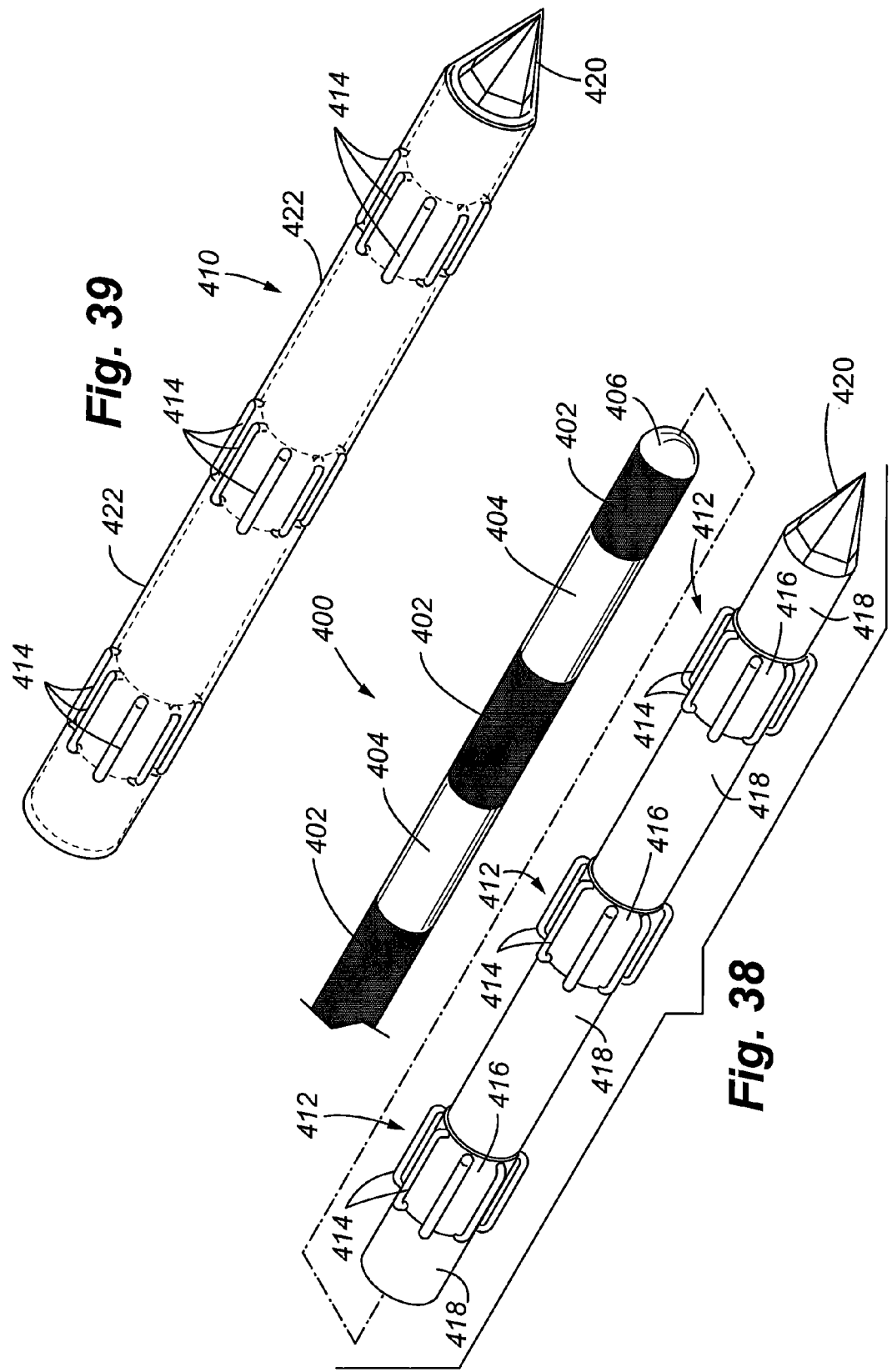

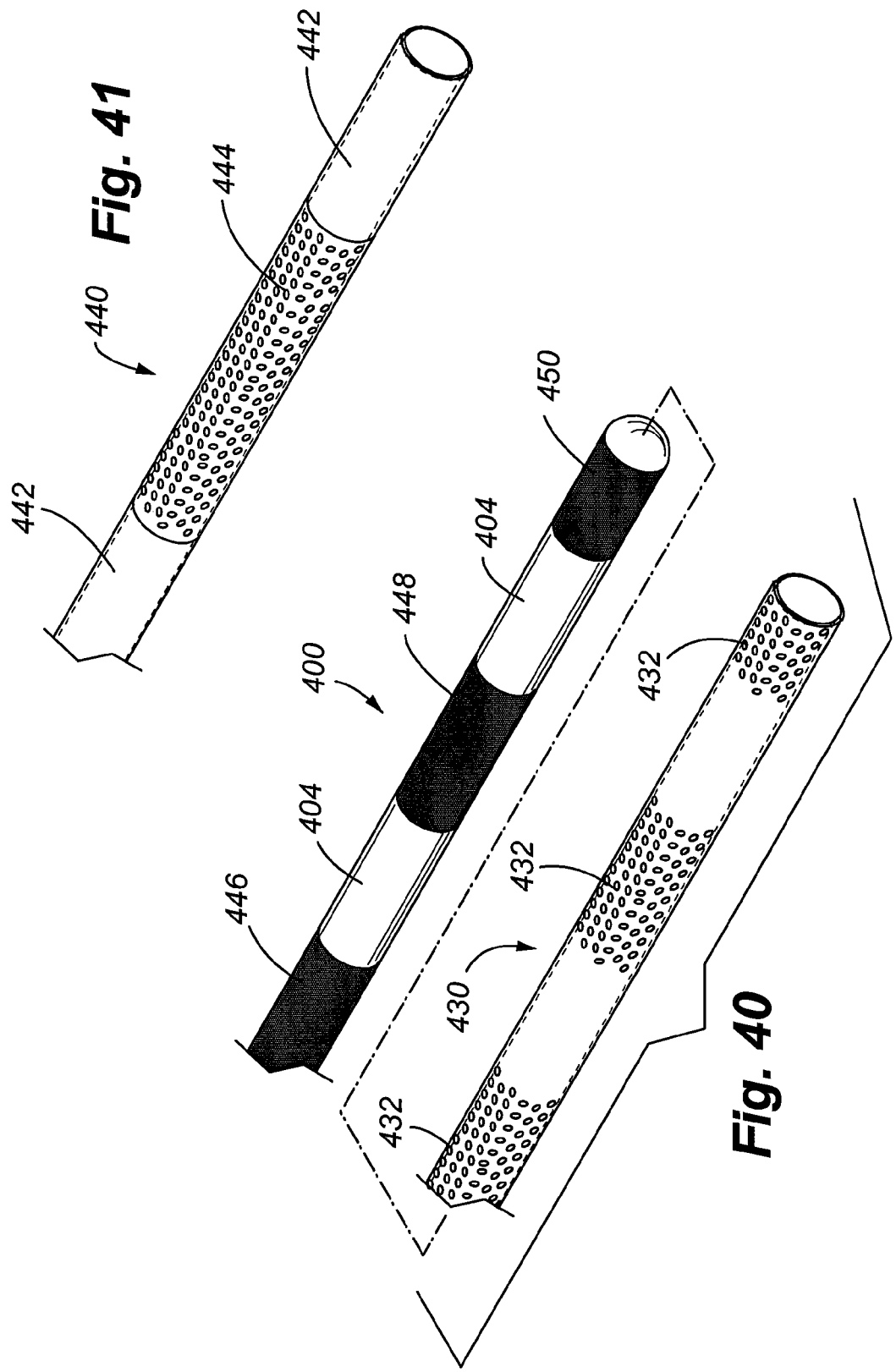

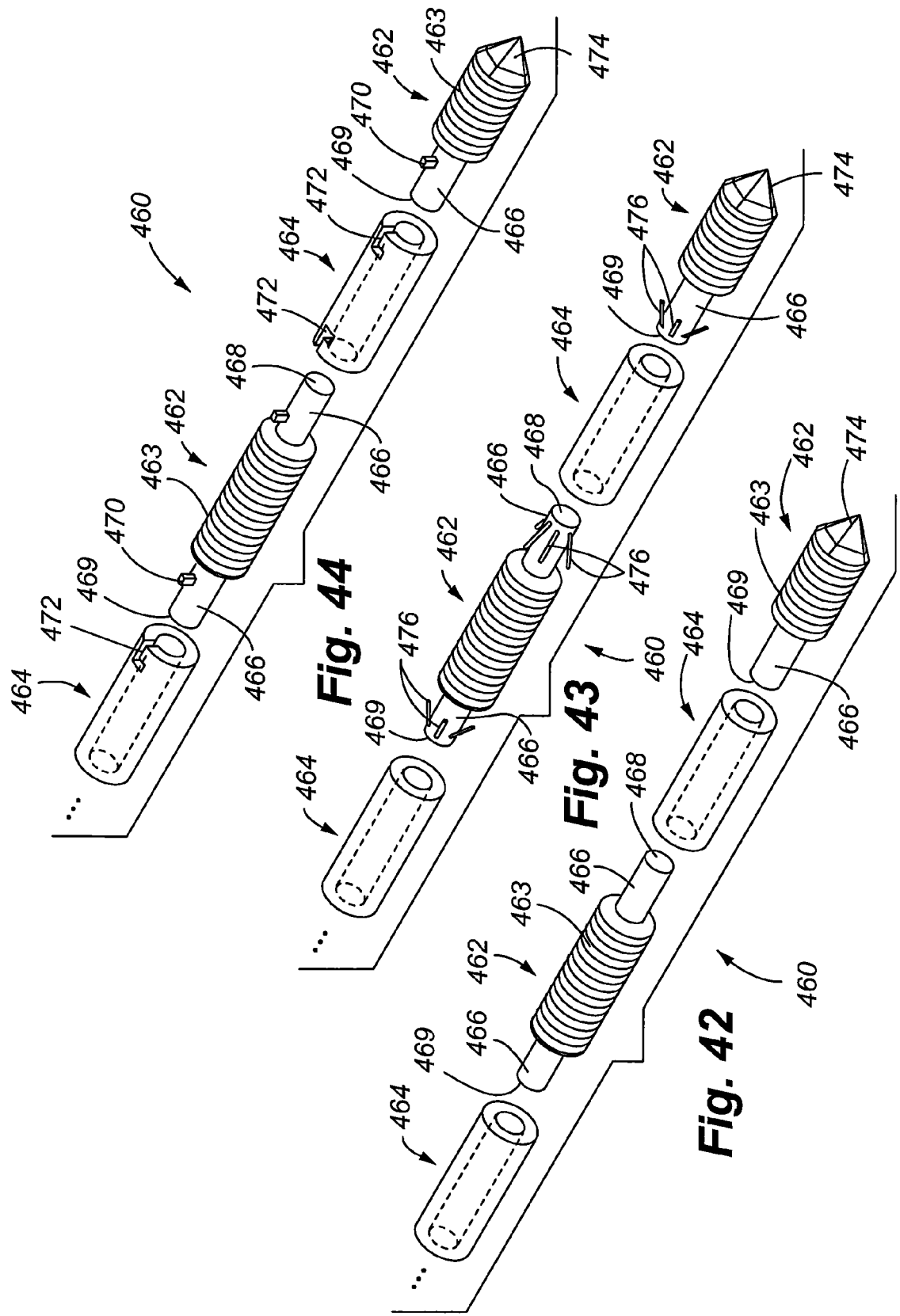

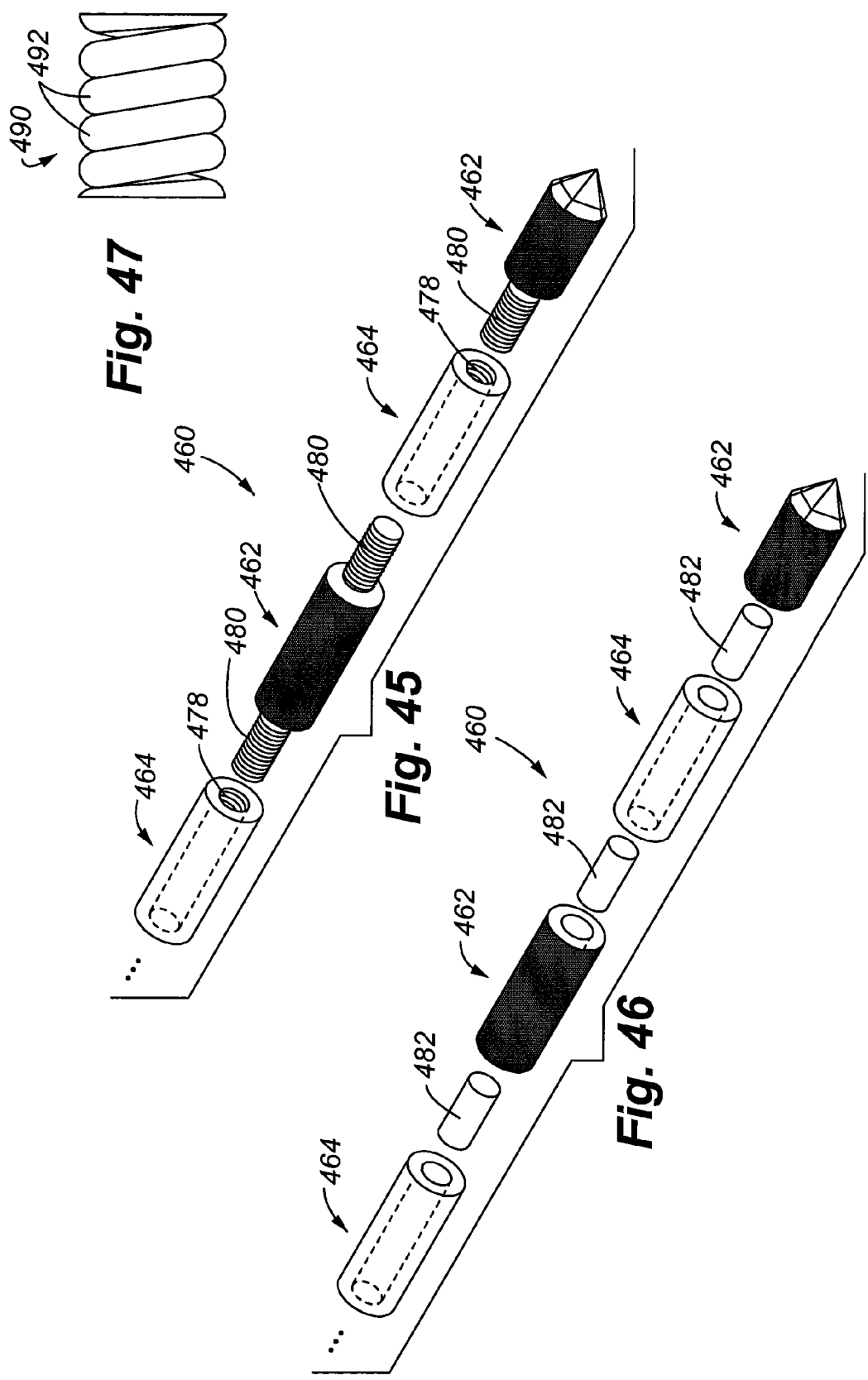

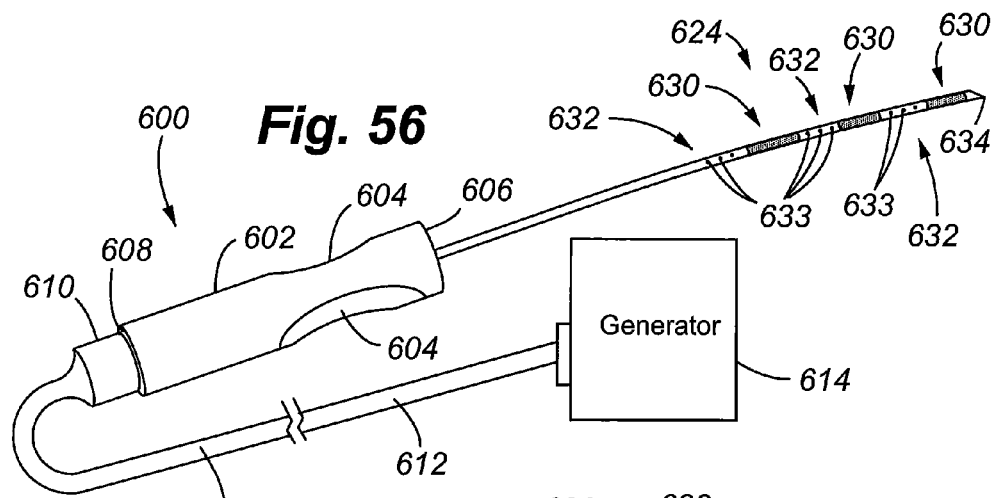
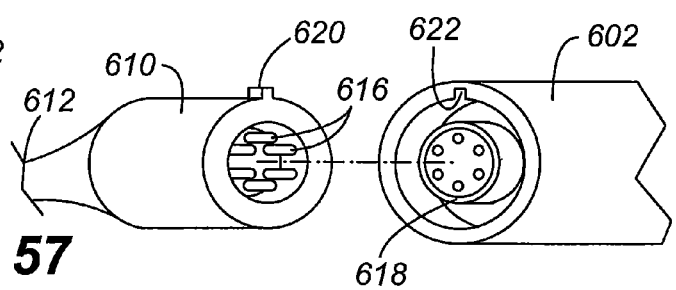
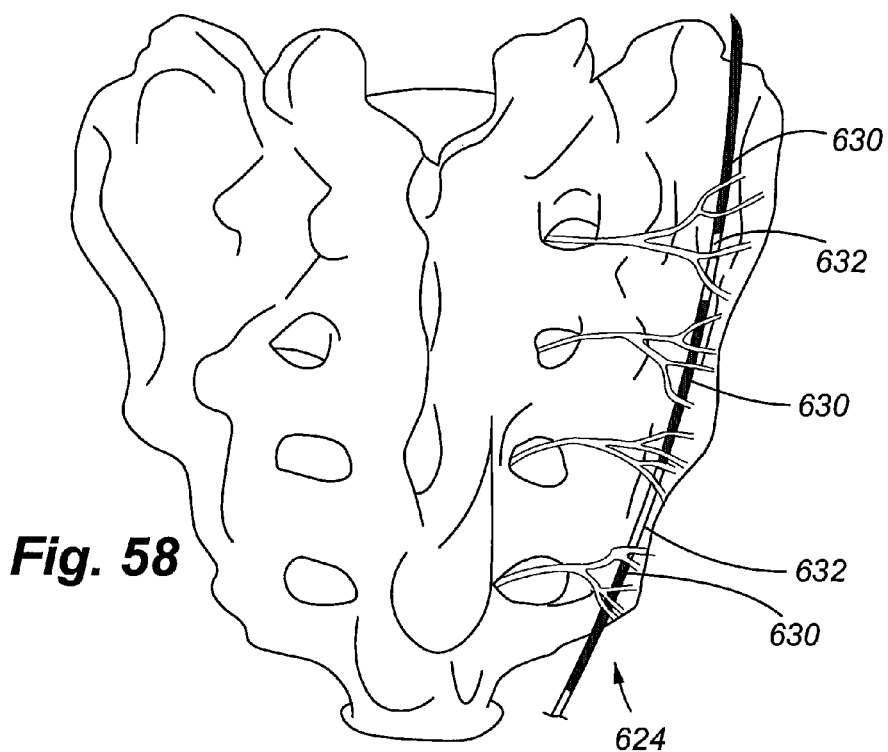

COMBINATION ELECTRICAL STIMULATING AND INFUSION METHOD

CROSS REFERENCE TO RELATED APPLICATION

This Application is a Divisional of U.S. patent application Ser. No. 12/033,232, filed on Feb. 19, 2008, now U.S. Pat. No. 8,066,702, entitled "COMBINATION ELECTRICAL STIMULATING AND INFUSION MEDICAL DEVICE", which is a Continuation-in-Part of application Ser. No. 11/678,516, filed on Feb. 23, 2007, now U.S. Pat. No. 7,945,331, entitled "COMBINATION ELECTRICAL STIMULATING AND INFUSION MEDICAL DEVICE", which is a Continuation-in-Part of application Ser. No. 11/033,591, filed on Jan. 11, 2005, now U.S. patent Ser. No. 11/033,591, entitled "COMBINATION ELECTRICAL STIMULATING AND INFUSION MEDICAL DEVICE", the disclosures of which are hereby incorporated by reference herein.

TECHNICAL FIELD OF THE INVENTION

The present invention relates generally to electrical stimulation leads and chemical infusion catheters for treatment of medical conditions, and more particularly, to a system, method and device for providing combined electrical stimulation and chemical/drug infusion for treatment of targeted tissue such as intervertebral discs, SI joints, various vertebral structures, and various nerve groups along the spine to include the spinal cord.

BACKGROUND OF THE INVENTION

It is known that immersing certain cell types within an electrical field will cause these cells to proliferate thus facilitating tissue repair. One known use of an electrical field for such repair is "in bone" stimulators that are implanted in fractures and/or spinal fusions. Another type of treatment has recently been developed for spinal conditions wherein target tissue is stimulated by an electrical lead using radio-frequency energy to induce a thermal lesion in the target tissue. In this type of procedure, the therapeutic benefit is intended to derive from heating the target tissue and not from immersing the tissue in an electric field. Thus, the electrical lead in this treatment is strictly for use in heating the tissue, and there is no therapeutic electrical field generated. Chemical treatment of target tissues has also been developed by use of various types of infusion catheters.

For both electrical and thermal stimulation, an electrical current generator, commonly referred to as a pulse generator, may be used to transmit a pulse of electrical current to an implanted stimulation lead that has been precisely placed to transmit the electrical or thermal energy from the electrodes to the target tissue in order to treat the particular condition. For chemical stimulation, one or more drugs or nutrients are delivered by a pump that transfers a desired quantity and frequency of the drug/nutrient through an infusion port of the catheter to the target tissue. For chemical stimulation as well as electrical/thermal stimulation, implanted pumps and generators can be used to deliver the electrical and chemical stimulation as opposed to trans-dermal delivery devices. More particularly, implanted pulse generators (IPG) as well as implanted drug dispensers (IDP) are commonly used so that patients do not have to return to a medical facility each time treatment is to be conducted.

The intervertebral disc (IVD) provides separation, shock absorption, and controlled motion between vertebral bodies. The disc is comprised of a central nucleus of a semi-fluid mass of mucoid material, (nucleus pulposus), an outer more dense collagen ring (annulus fibrosis), and a thin, metabolically active cellular layer separating the nucleus and the outer collagen ring, referred to as the annular nuclear interface/transitional zone. Disc nutrition is tenuous at best and is provided by diffusion through the vertebral end plate in contact with the outer surface of the disc. As a result, a disc has limited ability to heal or regenerate. Due to age, injury or other conditions, cracks or fissures may develop in the wall of invertebral discs causing a chronic source of pain in many patients. Additionally, the inner disc tissue (nucleus) will frequently cause the disc to bulge or herniate into the fissures in the outer region of the disc, thus causing nerve tissue therein to generate pain signals.

Current treatment for such disc disorders include analgesics, physical therapy and epidural steroid injections. Success with these treatments is frequently disappointing and the patient will all too often have to undergo spinal fusion. Spinal fusion is a very invasive, bio-mechanically altering, and marginally effective treatment.

One relatively new procedure has been developed to treat such disc ailments and general discogenic back pain. As an alternative to other surgical procedures for patients who suffer from back pain caused by certain types of disc disorders, this new procedure is made possible by use of thermal stimulation leads that provide precise temperature control in the delivery of thermal energy to target tissue. This procedure, commonly referred to as intradiscal electro-thermal annuloplasty (IDET) was initially believed to function by cauterizing nerve endings within the disc wall to assist in reduction of pain, and the heat produced by the stimulation leads would also thicken the collagen of the disc wall thereby promoting healing of the damaged disc. IDET has proven in some cases to be a minimally invasive procedure to treat these types of disc ailments. However, recent research, and clinical experience has cast doubt as to the exact method of action. More specifically, for percutaneous treatments like IDET, the general operating premise in these procedures, is to heat, either through conduction or induction, causing collagen restructuring and nociceptor coagulation within the disc that would stabilize the structure, and denervate the painful discs while retaining the motion segment and thus reduce the need for fusion. While these procedures have proven more effective than placebo, the results are far from acceptable. Research has demonstrated that collagen modulation and nociceptor coagulation is unlikely to be the mechanism of action, and that these devices may simply create injury patterns, that in a small subset of patients, stimulates a regenerative response, thereby accounting for the better than placebo results.

Combination electrical stimulators and chemical infusion catheters are known for purposes of treating various spine and brain ailments. One reference that discloses such a combination device is the invention in U.S. Publication No. US2004/0243206. This reference specifically discloses a combination electrical and stimulation lead for stimulation of a person's nerve tissue in the brain. One or more electrodes are located along the lead body and are adapted to be positioned proximate the target nerve tissue and to deliver electrical stimulation pulses transmitted through the lead to the target nerve tissue. One or more infusion ports located along the lead body are adapted for placement proximate the target nerve tissue and to deliver chemical stimulation pulses transmitted through the lead to the target nerve tissue.

While combination electrical and stimulation leads may be known, special considerations must be made for use of such devices for intervertebral disc treatment.

Placement of a stimulation lead within a disc can be quite difficult. Because a disc does not have a uniform density, known stimulation leads can be quite difficult to place and may require the attending physician to make multiple attempts for proper placement or abandon the procedure. Of course, multiple placement attempts greatly increase the invasive nature of the procedure and therefore create unnecessary tissue damage and increased risk. Inability to perform the procedure denies the patient a therapeutic option. Improper placement of the stimulation lead can also result in the undesirable damage of nerve tissue that is not contributing to the chronic pain or other ailments. Because of the overall metabolically inactive nature of the disc, it is also important that chemical infusion be precisely targeted to contact the damaged area of the disc with the delivered chemicals/nutrients, otherwise inaccurate delivery to non-damaged portions of the disc can reduce the effectiveness of the procedure. Thus, there is a need for a combination electrical and chemical stimulation lead that can be precisely placed with a high rate of success on a first attempt.

The IVD is also a motion segment of the body that is subjected to many flexion/extension/rotation cycles every day. In some procedures, it may be necessary to keep the stimulation lead emplaced for long periods of time, such as weeks or perhaps months. Thus, it is desirable to have a stimulation lead that maintains a small profile, yet is resilient enough to withstand the risk of permanent deformation or shearing during treatment and removal of the stimulation lead after treatment.

Many complaints of lower back and leg pain have been attributed to herniated disk related injuries to the spinal column. Extensive therapy and treatment is often unsuccessful in alleviating such pain since some of these problems are actually associated with symptomatic sacroiliac dysfunction or instability. Other terms to describe sacroiliac ailments include sacroiliac joint complex, sacroiliac joint dysfunction, and others. One reference that discloses the use of a bone implant to provide stability and compression for immobilization of the SI joint is the U.S. Pat. No. 6,053,916. One reference that discloses methods for treatment of pain caused by an SI joint dysfunction includes U.S. Pat. App. Publication No. US 2006/0217705. This reference discloses a number of electro-surgical devices in which energy is directed to a targeted region of tissue. A probe is inserted into the target site within the sacroiliac region of the patient's body and energy is delivered to the probe. At the location of the probe, the tissue is ablated thereby creating lesions. In the case of contact of the probe with neural tissues, denervation is achieved which therefore can reduce or eliminate pain associated with the particular dysfunction being treated.

With respect to neural ablation to alleviate symptomatic pain associated with numerous types of spine ailments, current stimulation leads are limited in the provision of ablative heat based on the size of the electrodes, their spacing along the lead, and their particular positioning relative to the targeted nerve group. In many instances, it may be necessary to move the stimulation lead during a procedure to cover all of the targeted tissue and repeatedly apply electrical energy to the lead. In other circumstances, it may be necessary for the introducer needle to be completely removed and reinserted in an adjacent position and then reposition the stimulation lead in order to cover the targeted tissue. Multiple lead position changes during a procedure of course increases the invasive nature of the procedure and also introduces additional risk of infection and that multiple needle insertions will damage non-targeted tissue.

While the prior art may disclose various devices and methods for treatment of targeted tissue throughout the body, there is still a need for improved devices and methods for treatment, to include devices and methods wherein electrical stimulation as well as chemical infusion may be provided with the same stimulation device. Additionally, there is a need for an electrical stimulation device that has the capability to provide various types of electrical stimulation and ablative patterns thereby increasing the chances that a procedure will be successful since the patterns can be selected to cover targeted tissue based on the condition of the particular patient and the ailment to be treated.

SUMMARY OF THE INVENTION

In accordance with the present invention, a combined electrical and chemical stimulation device is provided that is especially adapted for treatment of various types of ailments associated with the spine and nervous system.

With respect to treatment of an intervertebral disc, the stimulation device is in the form of a stimulation lead designed to be placed in the disc percutaneously through an introducer needle using an extra-pedicular approach; however, micro-surgical or open-surgical techniques may also be utilized. More specifically, the device of the present invention is specifically designed to facilitate placement proximate to the metabolically active cellular, nuclear, annular interface layer by use of one or more selected embodiments including a straight, curved or bent tip, as well as a variable stiffness tip. Selection of one of these embodiments allows the physician to precisely navigate the lead through the nucleus of the disc. In yet another embodiment of the present invention, the stimulation lead may be placed directly into the nuclear annular interface by use of an introducer needle having a bent tip, and use of a stimulation lead having a straight tip that can take a substantially linear path to reach the target tissue.

With respect to treatment of an SI joint, the same type of stimulation device used for treating the intervertebral disc can be used. Generally, the procedure for treatment of the SI joint involves first the placement of an introducer needle along the curvature of the sacrum with the needle tip ultimately advanced to the superior edge of the sacrum lateral to the sacral foramen and medial to the SI joint. The stimulation lead may be then placed through the introducer needle and advanced to the tip of the introducer needle. The introducer needle is then withdrawn along a specified length of the stimulation lead to expose the active number of contacts necessary to denervate the targeted sacral nerve lateral branches.

The structure of the stimulation lead of the present invention in some embodiments is characterized by an elongate and tubular shaped body including one or more electrodes located along selected portions of the lead body and adapted for positioning proximate the target tissue to deliver electrical stimulation pulses transmitted through the lead. In some embodiments, the electrodes extend circumferentially around a selected length or portion of the lead since it is difficult to orient a specific lateral side of the lead against target tissue. One or more infusion ports may also be located along the lead body and are adapted to be positioned proximate the target tissue to deliver selected chemicals/nutrients. In other embodiments, one large continuous electrode may cover the entire distal portion of the stimulation lead, and this type of lead is especially adapted for ablation procedures.

In some embodiments of the present invention, instead of a single tubular shaped body, the stimulation lead may have a plurality of lead elements with a common base, and the stimulation elements may be selectively deployed at the targeted tissue site. The separate stimulation elements may be deployed by a number of deployment mechanisms to include spring elements, hydraulic force, and selected materials with elastomeric and resilient characteristics that expand the lead elements in the desired configuration once it is freed from within an introducer needle or sheath. In yet other embodiments of the present invention, the stimulation elements may be flat or planar as opposed to tubular shaped. In some of the embodiments, a central stylet can be used to help guide the stimulation lead and to provide some additional rigidity to prevent inadvertent buckling or displacement of the lead.

Once the stimulation lead is correctly positioned, the lead is then connected to a pulse generator for delivery of electrical energy to the electrodes located on the distal portion of the stimulation lead. The electrical circuit can be completed by either use of a grounding pad placed on the patient or by the stimulation lead itself where the electrodes are provided in various combinations of anodes and cathodes. For those embodiments that include infusion ports, the lead may also be connected to an infusion pump that provides a controlled delivery of chemicals/nutrients through the lead to the target tissue. Preferably, the electrical pulse generator and infusion pump are implanted medical devices. These pulse generator and infusion pump devices are also preferably rechargeable and refillable. Another generally desirable characteristic of pulse generators includes those having a capability to produce either constant or variable current. It is also desirable to provide electrical contacts/electrodes that are linked in series, parallel, or combinations thereof which allow selective activation of all or a selected group of the electrodes. Other desirable general characteristics for an infusion pump are those pumps which (i) control infusion material at either a constant or variable rate, and at a constant or variable pressure, or constant or variable volume, (ii) provide automatic compensation for varying infusion pressures, and (iii) have anti-back flow capability to prevent backflow of infusion material through the stimulation lead, as well as pressure safety valves to compensate for overpressure situations. Furthermore, the pump, pulse generator and stimulation lead may be coated with an antibacterial coating to decrease the risk of infection. The pulse generator and pump may also incorporate appropriate alarms to notify of infusion and stimulation failure/abnormality.

Particular embodiments of the present invention provide one or more advantages in terms of navigation of the stimulation lead, as well as placement of the infusion ports and electrodes for effectively delivering electrical and chemical treatment. More specifically, the particular shape of the stimulation lead, as well as the particular placement of the electrodes and infusion ports are especially adapted for delivering the electrical stimulation and chemical infusion to target tissue. A stiffening or support element may be incorporated in the wall of the stimulation lead to ensure the lead does not prematurely shear or otherwise structurally fail during use and removal. The stiffening element is preferably in the form of an elongate support that extends longitudinally within the wall of the stimulation lead and terminating near the distal tip of the lead.

Other embodiments of the present invention provide advantages by use of a disposable sheath that can be used in combination with a reusable stimulation lead. The disposable sheath has electrical contacts forming the electrodes of the device when used. The reusable stimulation lead is placed inside the disposable sheath wherein the electrodes of the stimulation lead make electrical contact with the electrodes of the disposable sheath. Temperature sensing elements may be incorporated in the stimulation lead, such as thermocouples or RTDs in order to measure temperature at the active electrical areas to ensure uniform lesioning, and to otherwise provide additional safety to the procedure such that excessive energy is not applied. Since the disposable sheath is in thermal/electrical contact with the inner reusable stimulation lead, accurate temperature sensing can still take place when the temperature sensing elements are incorporated on the stimulation lead. It is also contemplated that temperature-sensing elements may be incorporated on the disposable sheath wherein the bundle of conductors from the temperature sensing elements are separately routed through the sheath.

Use of the disposable sheath allows great flexibility in determining the pattern, size, and general configuration of a stimulation lead to be used in many types of different medical procedures. By providing a reusable stimulation lead, the cost in conducting a procedure is reduced since only the disposable sheath is disposed of after use and not the entire assembly.

In yet another embodiment of the invention, an inflatable member may be used with a stimulation lead such that the inflatable member can shift or adjust the exact positioning of the stimulation lead to more accurately apply the electrical or thermal energy to the targeted area.

Further advantages and features of the present invention will become apparent from a review of the following detailed description, taken in conjunction with the drawings.

BRIEF DESCRIPTION OF THE DRAWINGS

Reference is now made to the following detailed description taken in conjunction with the accompanying drawings in order for a more thorough understanding of the present invention.

FIGS. 3-7 are greatly enlarged side or elevation views illustrating other preferred embodiments of the stimulation lead;

FIG. 8 is a greatly enlarged cross-section of the working distal portion of another preferred embodiment that incorporates a stiffening element;

FIG. 9 is a section taken along line 9-9 of FIG. 8;

FIG. 10 illustrates another preferred embodiment of the present invention in the form of an introducer needle having a bent distal end for placement of the stimulation lead directly into the nuclear annular interface of an intervertebral disc;

FIGS. 11-13 illustrate further embodiments of the present invention wherein the electrodes and infusion ports are dispersed substantially along the entire length of the stimulation lead;

FIG. 14 illustrates a cross section of a further embodiment of the present invention wherein a dual lumen is provided enabling greater selective control of infusion through designated portions of the stimulation lead;

FIG. 15 illustrates yet a further embodiment of the present invention wherein an inflatable member is provided near the distal end of the stimulation lead to help anchor the lead after emplacement;

FIG. 24 illustrates yet another preferred embodiment of the present invention showing a stimulation lead having a substantially uniform curvature along the length of the stimulation lead along with a bent distal tip;

FIG. 25 illustrates the embodiment of FIG. 24 wherein the stimulation lead is inserted adjacent a selected vertebral structure, for conducting treatment such as ablation of a ventral nerve group;

FIG. 26 illustrates yet another preferred embodiment of the present invention wherein the stimulation lead is substantially liner or straight, and a central needle or stylet is passed through a central lumen of the stimulation lead;

FIG. 29 is an exploded perspective view of a disposable outer sheath usable with a stimulation lead;

FIG. 30 is an assembled perspective view of the disposable sheath of FIG. 29;

FIG. 35 illustrates an enlarged exploded perspective view of various components of the disposable sheath and reusable stimulation leads of FIGS. 33 and 34, particularly showing construction details and the manner in which electrical connection is achieved between the electrodes of the outer sheath and stimulation lead;

FIG. 36 is a cross-section of the assembled disposable sheath of FIG. 66 showing the reusable stimulation lead of FIG. 33 used with the sheath; and FIG. 37 is another enlarged exploded perspective view of an alternate shaped bracket used to electrically interconnect the sheath to the stimulation lead.

FIG. 38 is a perspective view of a stimulation lead usable with another type of disposable sheath, wherein the electrical contacts/conductors are shown mounted to a mandrel during manufacturing;

FIG. 39 is a perspective view of a completed disposable sheath of FIG. 38;

FIG. 40 is a perspective view of yet another type of sheath usable with a stimulation lead;

FIG. 41 is a perspective view of a modification to the disposable sheath of FIG. 40;

FIG. 42 is an exploded perspective view of yet another preferred embodiment of a stimulation lead wherein the stimulation lead is assembled in sections;

FIG. 43 is a perspective view of a modification to the preferred embodiment shown in FIG. 42;

FIG. 44 is a perspective view of another modification to the stimulation lead shown in FIG. 42;

FIG. 45 is a perspective view of another modification to the stimulation lead shown in FIG. 42;

FIG. 46 is a perspective view of yet another embodiment showing a stimulation lead having sections interconnected by conductive pegs;

FIG. 47 is an enlarged elevation view of one type of electrode that may be used with the various preferred embodiments of the present invention;

FIG. 56 is a perspective view of yet another electrical stimulation device of the present invention;

FIG. 57 is an enlarged fragmentary exploded perspective view of one type of electrical connector that may be used to interconnect the stimulation device to an RF generator;

FIG. 58 is a posterior/dorsal view of the sacroiliac region with the stimulation lead of FIG. 56 positioned along the SI joint to denervate selected sacral nerves;

DETAILED DESCRIPTION

Figure 1:
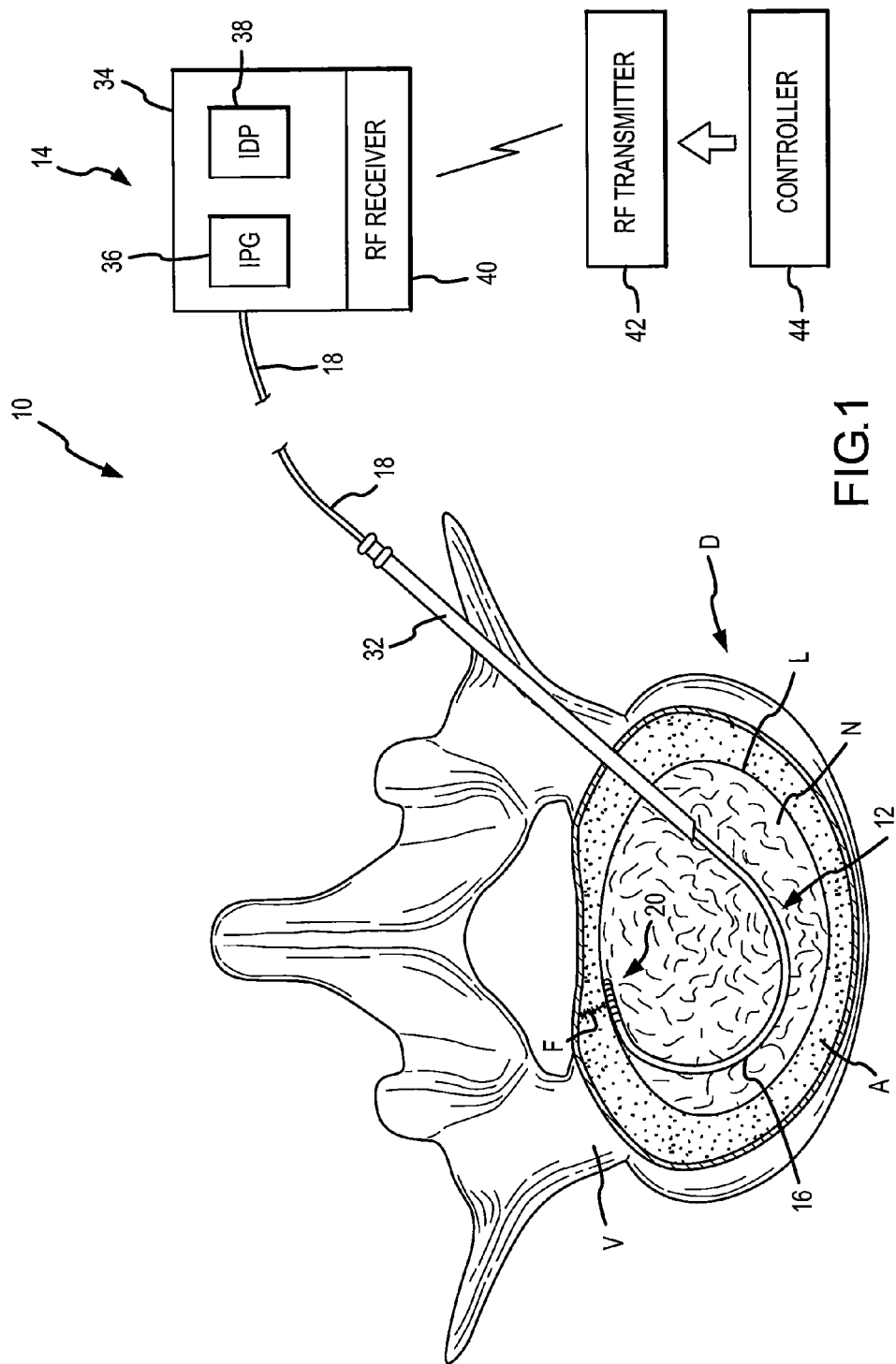
FIG. 1 illustrates the present invention including a stimulation lead inserted in an intervertebral disc, and a stimulation source that provides a controlled delivery of electrical field energy and chemicals/nutrients through the stimulation lead.
Figure 2:
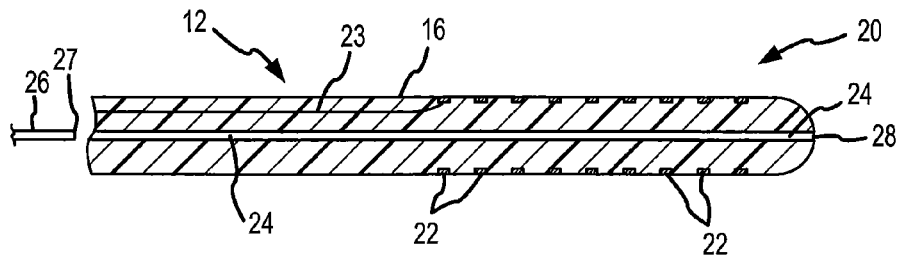
FIG. 2 is a greatly enlarged cross-section of the working distal portion of one preferred embodiment of the stimulation lead of the present invention.

Referring to FIGS. 1 and 2, the system 10 of the present invention is shown that includes a combination electrical and chemical stimulation device 12, a stimulation source 14 that communicates with the stimulation device 12 for delivering electrical energy and chemicals to the stimulation device, and an interventional device such as an introducer needle 32 that allows introduction of the stimulation lead. The stimulation device 12 is shown as inserted within an intervertebral disc D. The combination device 12 more particularly includes a percutaneous electrical and chemical stimulation lead 16 in the form of an elongate tubular member having a desired length and diameter allowing the lead 16 to be placed within the intervertebral disc of the patient to be treated. The working distal portion 20 of the stimulation lead 16 provides the desired stimulation through a plurality of electrodes 22 which are selectively positioned on the distal portion 20, along with a plurality of infusion ports 30 which allow delivery of chemicals/nutrients to target tissue. The proximal portion of the stimulation device 12 can be referred to as a lead extension 18 that connects to the stimulation source 14. The lead extension 18 can be made of the same type and diameter material as the stimulation lead 16, or may be made of a different type of material and diameter.

Referring specifically to FIG. 2, in a first embodiment of the stimulation lead, a plurality of circumferentially extending electrodes 22 are positioned at the distal portion 20. The electrodes 22 are also spaced longitudinally along the distal portion 20. The electrodes produce an array of electrical field energy, and the target tissue is immersed in the electrical field. One or more electrical conductors 23 extend through the interior of the stimulation lead 16 in order to transmit the electrical impulses to the electrodes 22. It is preferable to utilize a single conductor 23 along the major length of the lead, and then provide branch conductors (not shown) at the distal portion 20 that then extend to contact the various electrodes. The branch conductors could be a linearly arranged set of wire extensions extending between each electrode, or any other advantageous combination of wire conductors to interconnect the electrodes. Use of a single conductor is a more robust design as opposed to multiple smaller conductors that are more prone to breakage as a result of the motion cycles of the IVD. It is also contemplated that the electrode could be a single electrode wound in a helical pattern about the distal portion 20. Thus in this helical pattern, only one conductor 23 would be required with no additional branch conductors. In order to generate the desired intensity and size electrical field, the electrodes 22 can be disposed on the distal portion in a pattern or arrangement that best suits the electrical field to be generated. For example, in the helical pattern, the electrode could be wound with a tighter pattern to generate a more intense field, while a looser more spaced pattern would generate a less intense field. Of course, the particular signal or impulse current provided to the electrodes also determines the intensity of the field generated.

In order to provide chemical infusion, a central lumen or passageway 24 is formed through the stimulation lead. The central lumen 24 may extend completely through the lead thereby forming a distal opening 28 in the stimulation lead and providing one infusion port that is directed distally of the stimulation lead.

The stimulation lead 16 may be made of a homogeneous material, or may be made of differing materials that cause the stimulation lead to have either a more progressively stiff or more progressively flexible characteristic as the lead extends in the distal direction. Depending upon the manner in which the stimulation lead is to be emplaced, it may be desirable to use either the more progressively stiff or more progressively flexible arrangement.

In accordance with the method of the present invention, a stylet (not shown) is first inserted through the introducer needle 32. The introducer needle 32 is emplaced by penetrating the skin and muscle tissue, and ultimately into the disc D. When the introducer needle has penetrated the disc, the stylet is removed and the stimulation lead 16 is then inserted through the lumen of the introducer needle.

Referring again to FIG. 1, the stimulation lead 16 is illustrated as being emplaced within the disc D. This disc D is shown in cross section along with an adjacent vertebra V. The stimulation lead 16 is shown as taking an arcuate or curved path through the disc nucleus N in order to be precisely positioned at the area of the disc to be treated, illustrated as a fissure F which has developed adjacent the spinal fluid sac (not shown). The other primary features of the disk D are also illustrated including the annulus fibrosis A and the thin layer L defining the annular nuclear interface/transitional zone.

The stimulation source 14 is preferably an implantable medical device 34 including both an IPG (implantable pulse generator) 36 and an IDP (implantable drug dispenser) 38. The implantable device 34 could be contained within a single structural housing, or two separate housings, one for the IPG 36, and one for the IDP 38. The IPG and IDP can both be self-contained devices with internal control for preset delivery of electrical and chemical pulses. Alternatively, an external controller 44 could be used to modify the desired treatment protocol by use of RF transmission wherein an implantable RF receiver 40 is integrated with the IPG 36 and IDP 38. The RF receiver 40 could also be housed within the same implantable medical device 34, or could be a separate implanted device. An external RF transmitter 42 transmits RF signals to control the delivery of electrical stimulation and chemicals to the stimulation lead 16. A controller 44 provides the specific instruction set for transmission by the RF transmitter 42.

In accordance with the apparatus and method of the present invention, there are a number of nutrients and medications that can be delivered by the stimulation lead. For nutrients, this list includes, but is not limited to, glucose, glucosamine, chondroitin, oxygen and oxygenating agents, anti-oxidants, anti-glycosylating agents, and pH buffers. For medications, these may include, without limitation, anti-inflammatory agents and growth factors, such as growth and differentiating factor-5 (GDF-5), transforming growth factor-beta (TGF-$\beta$), insulin-like growth factor-1 (IGF-1), and basic fibroblasts growth factor (bFGF). In terms of the types of electrical impulses provided to the electrodes 22, these electrical impulses may be continuous or variable over time, and may vary based upon voltage, amperage, and alternate current frequency.

Figure 3:
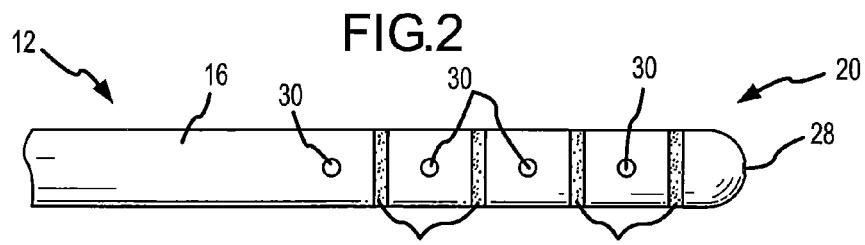

Referring to FIG. 3, a different arrangement is illustrated with respect to the location of the electrodes 22, and the single infusion port at distal opening 28 is supplemented with a plurality of additional infusion ports 30. In this embodiment, fewer electrodes are incorporated, yet additional infusion ports 30 are provided that are spaced longitudinally along the length of the lead 16 and placed between the electrodes 22.

Figure 4:
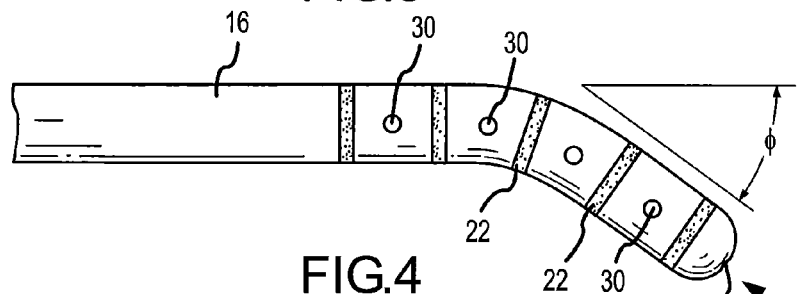

FIG. 4 shows another embodiment with a different arrangement of electrodes 22 and infusion ports 30 as well as a modification of the stimulation lead shape to include a bent distal tip having a chosen bend angle Ø. The bend angle Ø helps define the path of travel of the lead within the disc nucleus during emplacement. In other words, imparting a particular bend angle on the distal tip of the stimulation lead causes the stimulation lead to travel in an arcuate path such as shown in FIG. 1. Imparting a greater bend angle on the lead results in the stimulation lead traveling in a tighter arcuate path, while imparting a lesser bend angle generally results in the stimulation lead traveling in a broader arc or arcuate path.

Figure 5:
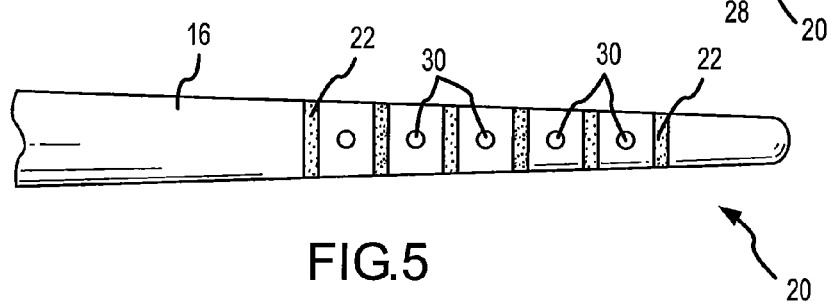

Referring to FIG. 5, another embodiment of the stimulation lead is illustrated wherein the lead has a progressively narrowing diameter towards the distal end thereof. With this type of stimulation lead, travel of the lead through the more dense annulus tissue is facilitated because the distal tip has a smaller frontal profile and is more easily controlled.

Figure 6:
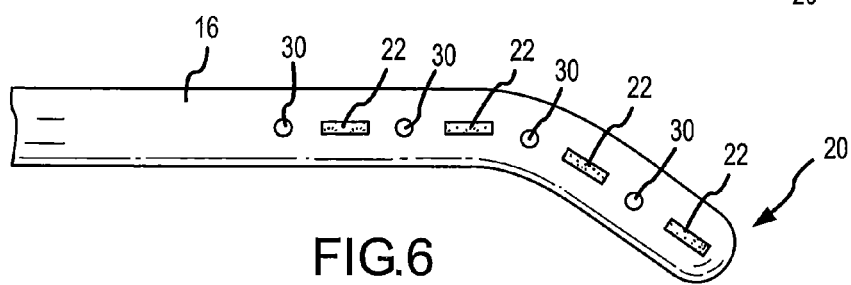

Referring to FIG. 6, yet another embodiment of the stimulation lead is illustrated wherein the electrodes 22 are not formed circumferentially around the distal portion 20, but are formed more linearly along one side of the stimulation lead. Additionally, the infusion ports 30 may have more of an oval shape and be larger in size that facilitates greater volumetric infusion. This embodiment may be preferred when it is desired to more precisely direct the array of electrical energy to the target tissue. The electrical energy array that is created by circumferentially arranged electrodes result in transmission patterns having a radial or circular pattern extending away from the stimulation lead. Thus, a plurality of circumferentially arranged electrodes transmit energy in all directions to tissue that surrounds the stimulation lead. On the contrary, locating the electrodes only along one side or edge of the stimulation lead results in transmission of energy in a more linear and less radial pattern, and directed primarily orthogonal or perpendicular to the axis of the stimulation lead. The embodiment of FIG. 6 also illustrates the distal end as being bent at a desired angle.

FIG. 7 illustrates yet another embodiment of the stimulation lead wherein the electrodes 22 are concentrated at a particular location, and the infusion ports 30 are spaced in a pattern extending a greater longitudinal length of the lead. A stimulation lead in this particular arrangement may be particularly suitable for repair of a fissure located at a very defined position within the disc, yet if the disc shows great overall degeneration, it is preferable to provide nutrients to a greater length of the annulus whereby the infusion ports 30 can distribute nutrients to a greater length of the annulus.

FIG. 8 illustrates yet another preferred embodiment of the present invention wherein a stiffening or strengthening member 47 is incorporated within the structural wall of the stimulation lead to provide increased strength to the lead without enlarging the frontal profile of the lead. As shown, the stiffening member 47 is an elongate member that extends longitudinally through the wall of the lead and terminates near the distal end thereof. The stiffening member is malleable to a degree that allows the lead to maintain some desired flexibility during emplacement, but increases the overall shear and torsional strength of the lead to prevent premature failure after emplacement or during removal. The member 47 could be made of a selected metal or thermoplastic, or of various synthetic materials such as Kevlar® and nylon, that are approved for medical use.

Referring to FIG. 10, yet another embodiment of the invention is shown wherein an introducer needle 46 is not placed within the disc nucleus, but rather is placed only into the disc annulus, and then the stimulation lead 16 extends through the disc annulus to the target tissue, also shown as a fissure F. In this embodiment, it is preferable that the stimulation lead 16 exits the introducer needle through a bent distal portion 48 so that the lead travels in a more parallel fashion within the annulus and along a more linear path to the target tissue. In the event the distal opening 28 of the lead 16 is of a size which could allow nuclear tissue to clog or block the distal opening 28, a guide wire 26 (see FIG. 12) may be inserted through the lumen 24 of the lead 16, and the distal tip 27 of the guide wire could be placed flush with the distal opening 28 in order to prevent clogging of the distal opening 28, as well as to provide additional rigidity for placement of the stimulation lead 16. If the guide wire 26 is used, then the guide wire 26 is removed prior to connecting the stimulation lead 16 to an IDP and/or IPG. Also, the central lumen may terminate before passing through the distal tip of the lead. Thus, all of the infusion ports 30 would be arranged on the lead to direct chemicals/nutrients in a perpendicular direction away from the axis of the lead.

FIGS. 11-13 illustrate yet further embodiments of the present invention wherein the electrodes 22 and infusion ports 30 are dispersed along substantially the entire length of the stimulation lead. In many cases, the disc to be treated has undergone such great degeneration that the entire disc is in need of treatment, as opposed to a more minor degenerative condition such as a single localized fissure. In such cases, it is advantageous to provide both electrical and chemical stimulation to as much of the disc as possible. The embodiments at FIGS. 11-13 show various combinations of the electrodes 22 and ports 30 that provide greater dispersion of the electrical and chemical stimulation. Specifically, the electrodes are larger and are spread out along a greater length of the lead. The infusion ports are also spread out along a greater length of the lead.

FIG. 14 illustrates yet another embodiment of the invention wherein a second lumen 41 is incorporated within the stimulation lead to provide greater infusion selectivity. More specifically, FIG. 14 shows that the second lumen 41 terminates at end 39 which is intermediate between the distal tip of the stimulation lead and the proximal end thereof. This lumen 41 communicates with the set of infusion ports 37 which are spaced from the end 39 of the lumen 41 towards the proximal end of the lead. The first or central lumen 24 then communicates with the infusion ports 35 that are located distally of the end 39 of the second lumen 41.

During treatment, it may be desirable to administer nutrients and/or medications to different parts of the disc being treated. Furthermore, it may be desirable to provide the nutrients/medications to these different locations within the disc at differing flow rates and at differing times and frequencies. With the provision of a dual set of lumens, a physician has the ability to selectively control infusion to two distinct areas within the disc, and can vary the treatment protocol between the two areas of the disc by selecting the particular dosing, frequency, and makeup of the infusion material to the distinct locations within the disc. This selective treatment capability may be advantageous where, for example, the distal end of the stimulation lead may be placed near the interface/transitional zone, and the tissue extending there along together with the annulus fibrosis may have particular needs in terms of the required type of nutrients and/or medication, while the tissue within the nucleus may have slightly different needs. Thus, the embodiment at FIG. 14 provides the treating physician with additional options in providing effective treatment.

The particular sizes of the lumens, as well as the sizes and spacing of the openings 35 and 37 may be configured for optimal delivery of various types of infusion material. For example, assuming that the desired nutrient/medication to be delivered to the distal end of the stimulation lead was fairly viscous, it may be advantageous to provide the lumen 24 with a larger cross-sectional size, as well as to provide the infusion openings 35 of an increased size to accommodate the higher viscosity. As a further example, if the lumen 41 was to deliver a less viscous nutrient/medication, then the lumen 41 would preferably have a smaller cross-sectional area, and the openings 37 would preferably be smaller than the openings 35. Thus, one convenient way in which to control infusion is to advantageously arrange the particular size, number, and spacing of the infusion openings as well as the size of the lumens that deliver the infusion material through the openings.

It is further contemplated within the present invention to also provide non-uniform lumens, as well as infusion openings that vary in size within the same supplying lumen. As discussed above, the IDP 38 may be programmed for preset delivery of chemical "pulses". The IDP 38 is typically programmed to be in an "on" or "off" state to generate delivery of a set amount of fluid over a specific period of time. However, once the infusion material is released from the IDP, the IDP itself does not have control over the way in which the infusion material is dispersed through the stimulation lead. Assuming that a lumen of a stimulation lead has a uniform diameter with infusion openings also being of a uniform diameter, then the infusion ports located at the more proximal end of the device will most likely deliver a greater amount of material to the disc as opposed to the infusion ports located at the distal end of the device because there will be an inherent loss in the amount of fluid delivered downstream based on frictional losses within the lumen and the upstream openings communicating with the lumen. Therefore, in order to ensure equal distribution of infused material, it may be desirable to provide a lumen having a diameter that progressively enlarges as it extends towards the distal end of the device. Alternatively or in combination with the progressively changing lumen size, it may be desirable to provide infusion ports toward the proximal end of the device that are slightly smaller than the infusion ports located towards the distal end of the device to further help compensate for any frictional line losses.

Referring to FIG. 15, yet another embodiment of the present invention is provided which further includes an inflatable portion 50 in the form of a bladder or balloon that is selectively inflated or deflated by an inflation line 52 extending conterminously with the central lumen. The inflatable portion is mounted to the exterior surface of the stimulation lead, and the inflation line 52 extends through an opening (not shown) in the sidewall of the lead that is covered by the inflatable portion 50. The inflation line 52 communicates with a source of compressed fluid (not shown), and the physician may inflate the inflatable portion 50 to a desired size. As also shown, the inflatable portion 50 is preferably placed along a location of the stimulation lead that does not cover or block any infusion ports 30, as well as any electrodes 22.

Figure 16:
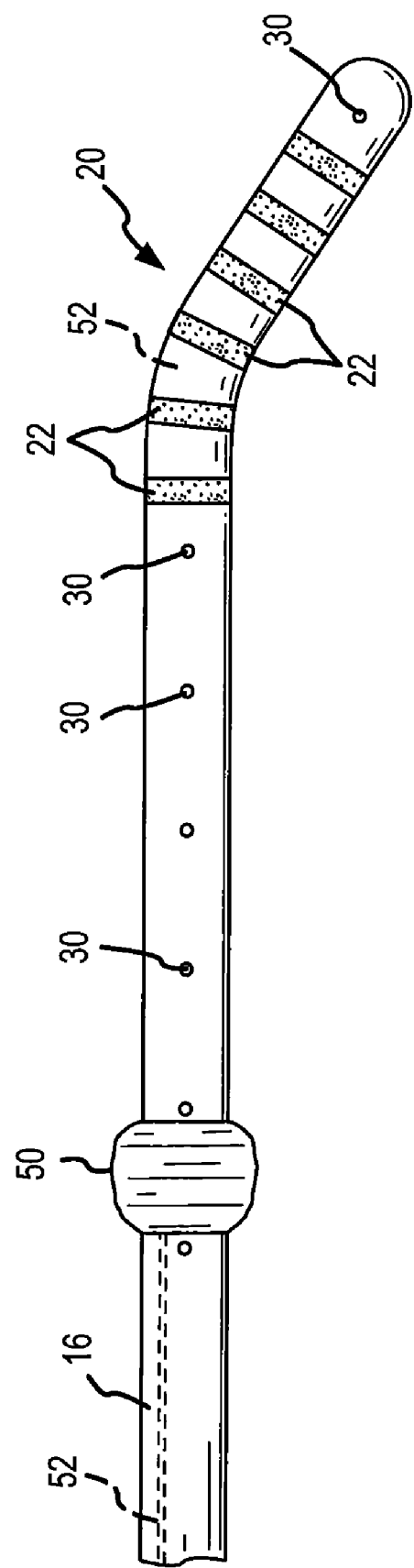
FIG. 16 illustrates the embodiment of FIG. 15 but the inflatable member being provided near the proximal end of the stimulation lead.

In some instances, the stimulation lead may reside within a patient for an extended period of time. As time passes, the stimulation lead may have a tendency to migrate or drift within the disc. Drifting of the stimulation lead can be problematic for a number of reasons, to include causing damage to the disc by penetration of the distal tip of the stimulation lead completely through the disc, as well as drifting of the stimulation lead so that it is no longer centered around/along the desired area of the disc to be treated. To maintain the stimulation lead in its desired position after the stimulation has been emplaced, the inflatable portion 50 may be inflated to the desired size, thereby serving as an anchor to help prevent drifting of the stimulation lead within the disc. In most instances, it is desirable to place the inflatable portion 50 near the distal tip of the stimulation lead to best prevent undesired drift of the stimulation lead; however, it is also contemplated within the present invention that the inflatable portion 50 may be selectively placed along other areas of the stimulation lead to best serve as an anchor. For example, as shown in FIG. 16, the inflatable portion is located at the proximal end of the stimulation lead. Furthermore, it may be desirable to incorporate both a distally located inflation portion 50, and another inflation portion located at the proximal end of the device that would further help to prevent the stimulation lead from drifting or from being inadvertently removed.

Some disc tissue may have a tendency to adhere to a stimulation lead that has been emplaced within the disc for a long period of time, and/or the disc tissue may have a tendency to harden around the emplaced stimulation lead thereby making it more difficult to remove the stimulation lead. Thus, it is also contemplated within the present invention that the inflatable portion 50 could be provided to extend along a much greater distance of the stimulation lead, and the inflatable portion 50 could be inflated to a desired level prior to the stimulation lead being emplaced within a disc. When it is then desired to remove the stimulation lead, the inflatable portion could be deflated which would create a small gap or space between the surrounding disc tissue and the stimulation lead thereby easing removal of the stimulation lead.

Thus, the inflatable portion 50 can be used either as an anchor to maintain positioning of the stimulation lead within the disc, or the inflatable portion 50 can be used in a reverse role by enlarging the overall size of the stimulation lead once emplaced, but then reducing the overall size of the stimulation lead by deflating the inflatable portion when it is desired to remove the stimulation lead.

Figure 17:
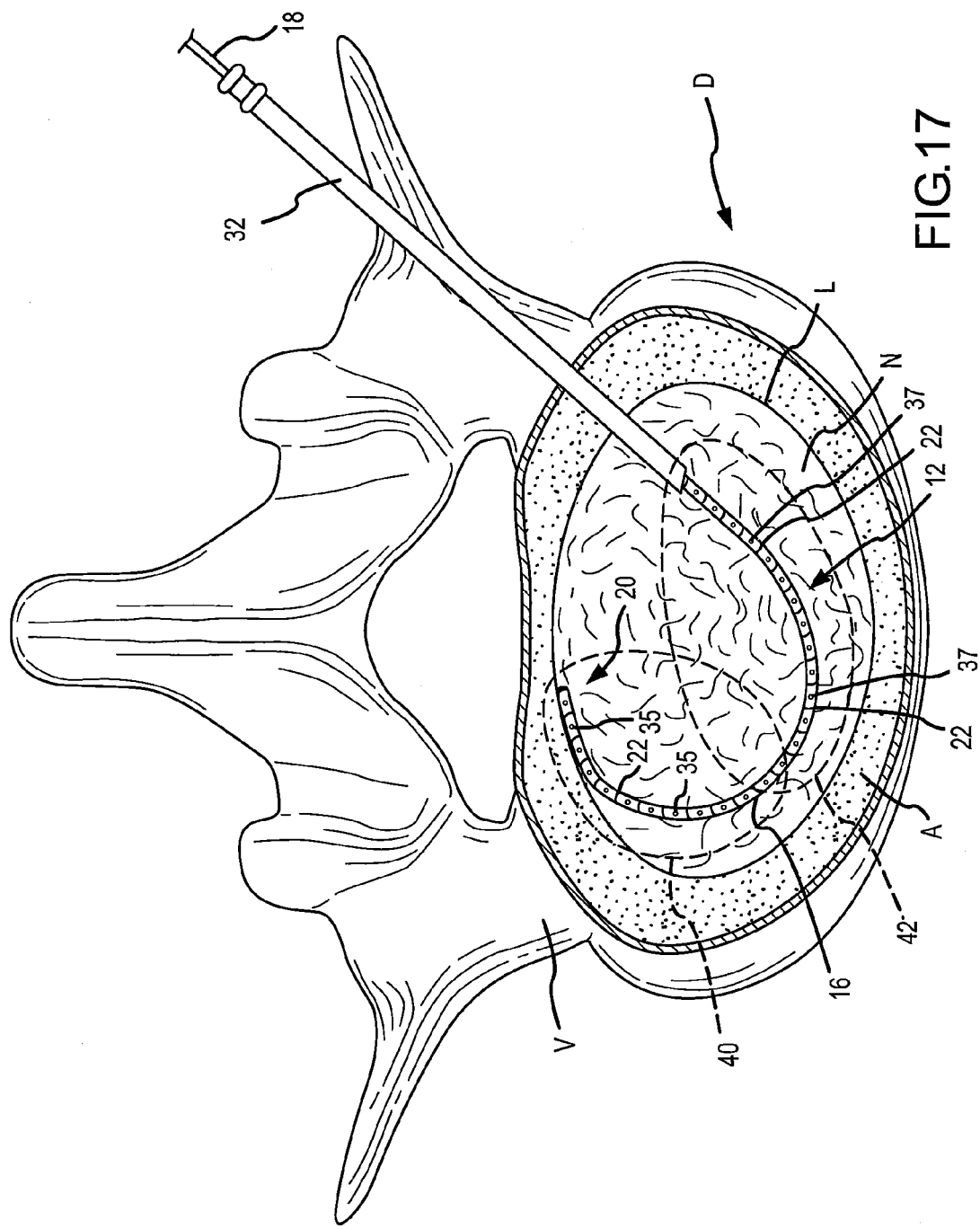
FIG. 17 illustrates the stimulation lead of FIG. 14 inserted in an intervertebral disc wherein the lead can selectively treat two targeted treatment zones or areas within the disc.

Referring to FIG. 17, a stimulation lead is shown emplaced within a disc D, the stimulation lead generally corresponding to the embodiment shown in FIG. 14. Two oval shaped areas 40 and 42 are shown surrounding the distal and proximal sections of the stimulation lead, respectively. These areas 40 and 42 may generally represent targeted treatment areas within the disc. In accordance with the embodiment of FIG. 14, the physician has the option of applying different infusion materials through the separate sets of infusion ports 35 and 37 to specifically target the tissue located within the areas 40 and 42. Such treatment could be simultaneous, sequential, or any combination thereof. Furthermore, as mentioned above, selected sets of electrodes could be energized to provide treatment. For example, the electrodes may be wired so that the physician has the ability to energize two primary sets of electrodes, one set providing an electromagnetic field generated to cover area 40, and the other set providing an electromagnetic field to cover area 42. The electrodes may be wired and configured to provide generation of electromagnetic fields in any desired pattern along the length of the lead.

Figure 18:
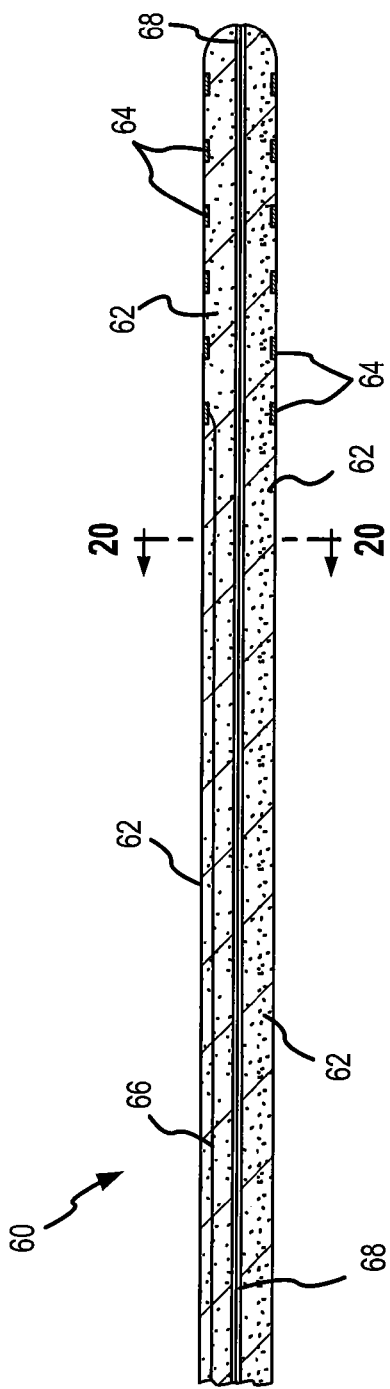
FIG. 18 illustrates a cross section of yet a further embodiment of the present invention wherein the body of the stimulation lead is made from a dissolvable matrix with the stimulating electrical contacts embedded therein.
Figure 19:
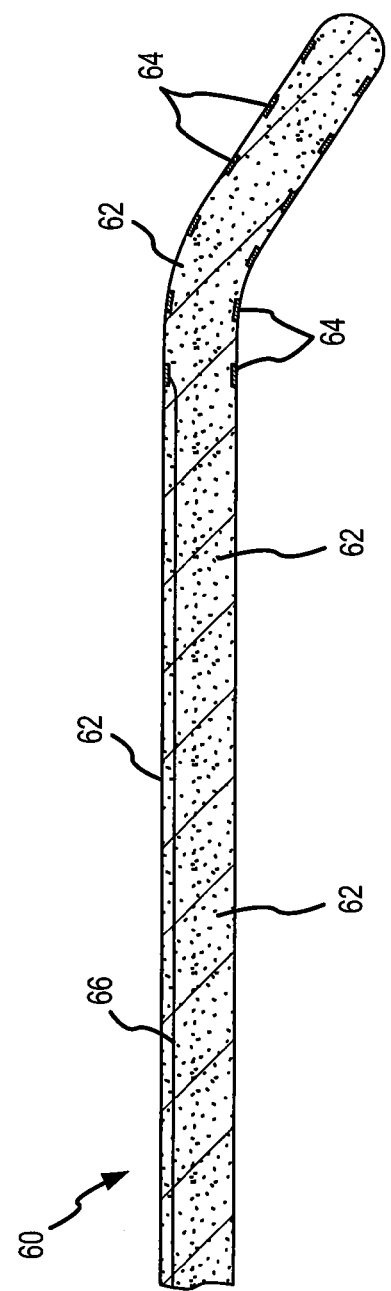
FIG. 19 illustrates a cross section of a further variation of the embodiment of FIG. 18 wherein the stimulation lead has a preconfigured bend at the distal end thereof and no central lumen.
Figure 20:
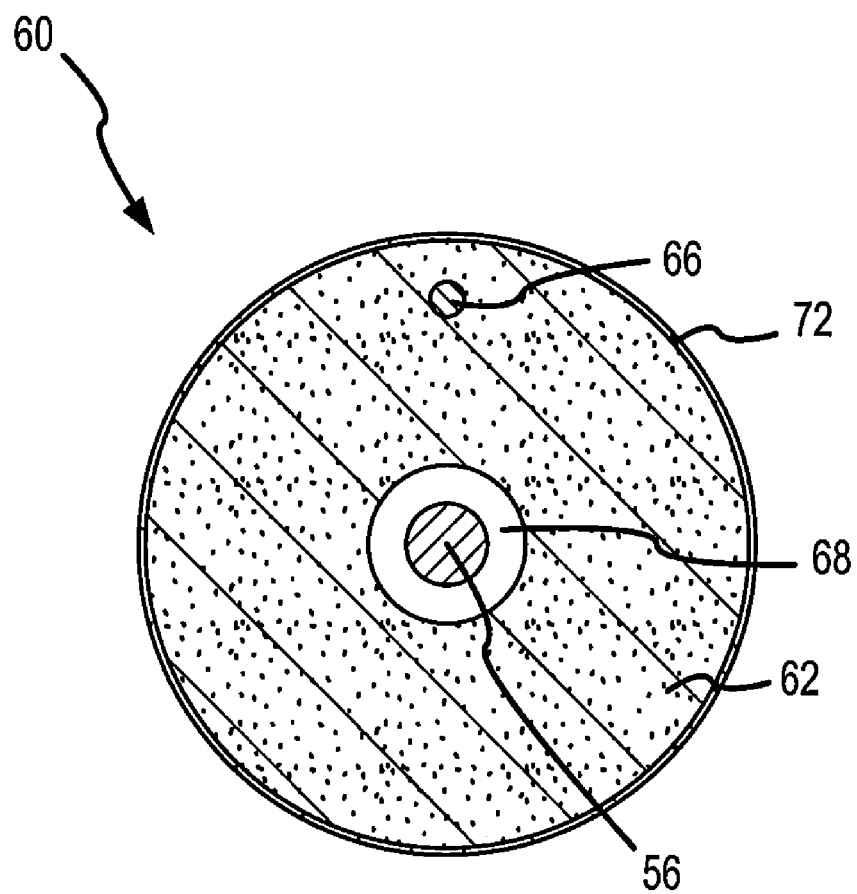
FIG. 20 is a cross-section taken along line 20-20 of FIG. 18, and further illustrating the use of an outer membrane which may help maintain the integrity of the stimulation lead when emplaced, as well as to control the rate at which the constituents incorporated within the dissolvable matrix are allowed to diffuse into the intervertebral disc.

Referring now to FIGS. 18-20, yet another embodiment of the present invention is illustrated in the form of stimulation lead 60. For some treatments, it may be necessary to leave the stimulation lead emplaced within the invertebral disc for an extended period of time; however, for various reasons, it may not be possible to keep the stimulation lead emplaced for the amount of time to provide optimal treatment. In order to solve this particular problem, the embodiment of FIG. 18 contemplates the use of various chemical agents/medications and nutrients incorporated within a dissolvable matrix that forms the body 62 of the stimulation lead 60. The electrodes 64 as well as the conductor(s) 66 could be formed with the dissolvable matrix in a molding process whereby a particular shape and size stimulation lead could be produced. The electrodes 64 could function the same as the electrodes 22 discussed above and could be produced in any desired pattern and wiring arrangement. The dissolvable matrix can be made of a material that is biomedically acceptable for enabling a time release of the chemical agents/medications and nutrients mixed within the matrix. The matrix is preferably a solid yet flexible material, allowing the stimulation lead to be steered with the use of an insertable stylet 56 which could be provided through the central lumen 68. However, it shall be understood that this central lumen 68 is optional, and the matrix may be manufactured of a material which is durable yet flexible enough allowing the practitioner to steer the stimulation lead without the use of a stylet. Accordingly, FIG. 19 illustrates another embodiment wherein there is no lumen present, and a predetermined bend angle is formed in the stimulation lead enabling the lead to take the desired path through the disc when emplaced. Once inserted into the disc, the matrix would dissolve and the regenerating chemicals/medications and nutrients would slowly diffuse into the surrounding disc tissue leaving only the electrodes 64 and conducting wire(s) 66 to be removed at some later time.

With the embodiment shown in FIGS. 18 and 19, an infusion pump would not be required, and would thereby also allow for the subcutaneously placed pulse generator (IPG) to be significantly smaller. Similar to the combined pump/pulse generator device described above, this much smaller pulse generator could be rechargeable, or be powered by a battery source as desired.

In a modification to the embodiment of FIG. 18, it is also contemplated within the scope of the present invention that a stimulation lead can simply comprise a dissolvable matrix having a desired combination of chemical agents/medications and nutrients, and no electrodes incorporated within the lead. In some cases, stimulation by an electromagnetic field may be unnecessary to achieve the desired regenerative and/or pain relieving disc response.

FIG. 20 illustrates the designated cross-section of the device in FIG. 18. Additionally, FIG. 20 illustrates the use of an optional outer membrane 72 which could serve multiple purposes. One purpose for the membrane 72 would be to support the structural integrity of the matrix material of the body 62, thereby providing additional support for when the stimulation lead was emplaced. Additionally, this membrane 72 could serve as an osmotic membrane to help meter the rate at which the chemical agents/medications and nutrients were allowed to diffuse into the surrounding tissue. Thus, in addition to the matrix having a predetermined rate of diffusion, the membrane 72 could be used as an additional means to control the rate at which the chemical agents/medications and nutrients were delivered to the surrounding tissue. It is further contemplated that if the membrane 72 is provided only for structural support to the lead when emplaced, the membrane could be made of a material that quickly dissolves after being emplaced within the disc and the diffusion rate would be entirely controlled by the particular diffusion characteristics of the matrix.

Figure 21:
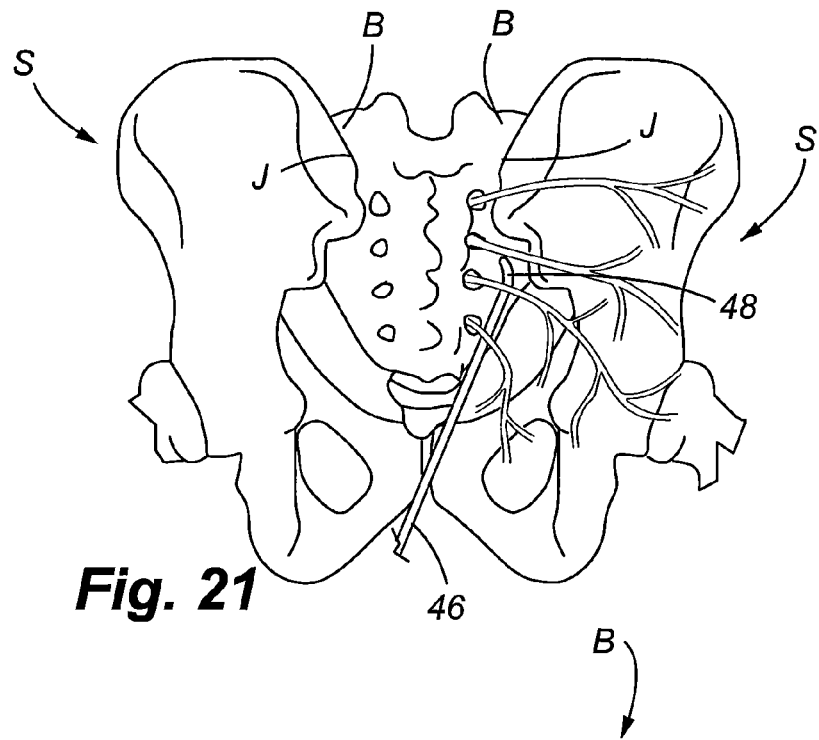
FIG. 21 is a posterior/dorsal view of the sacroiliac region with an introducer needle being positioned for insertion along the SI joint.
Figure 22:
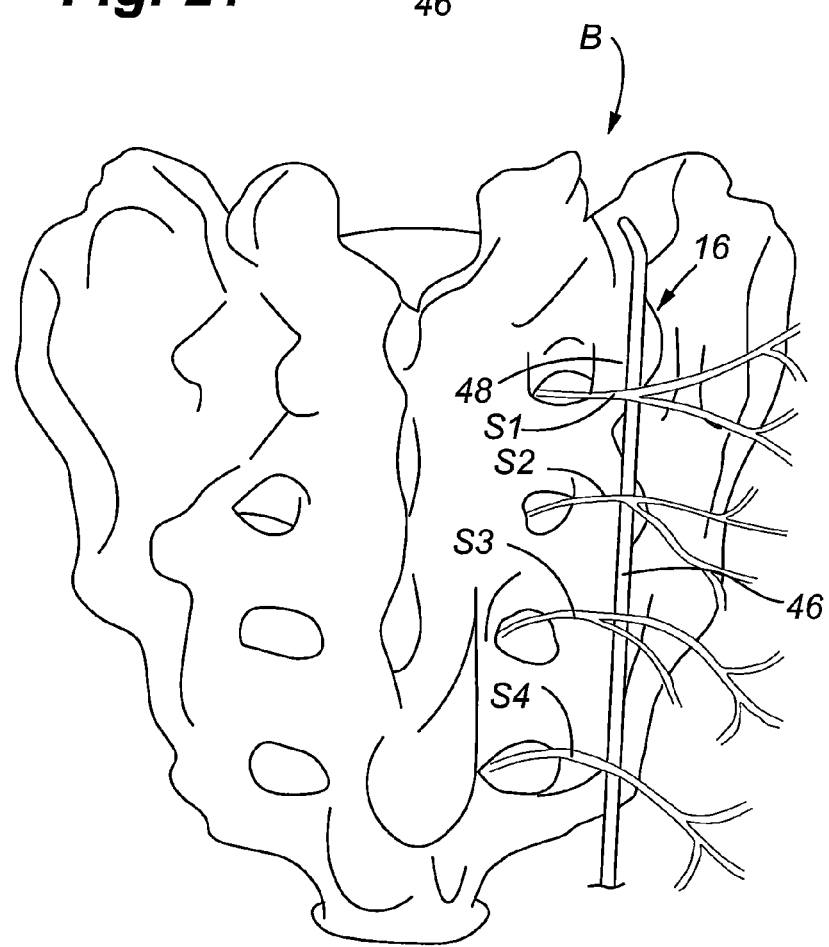
FIG. 22 is an enlarged posterior/dorsal view of the sacrum bone showing the introducer needle fully inserted.
Figure 23:
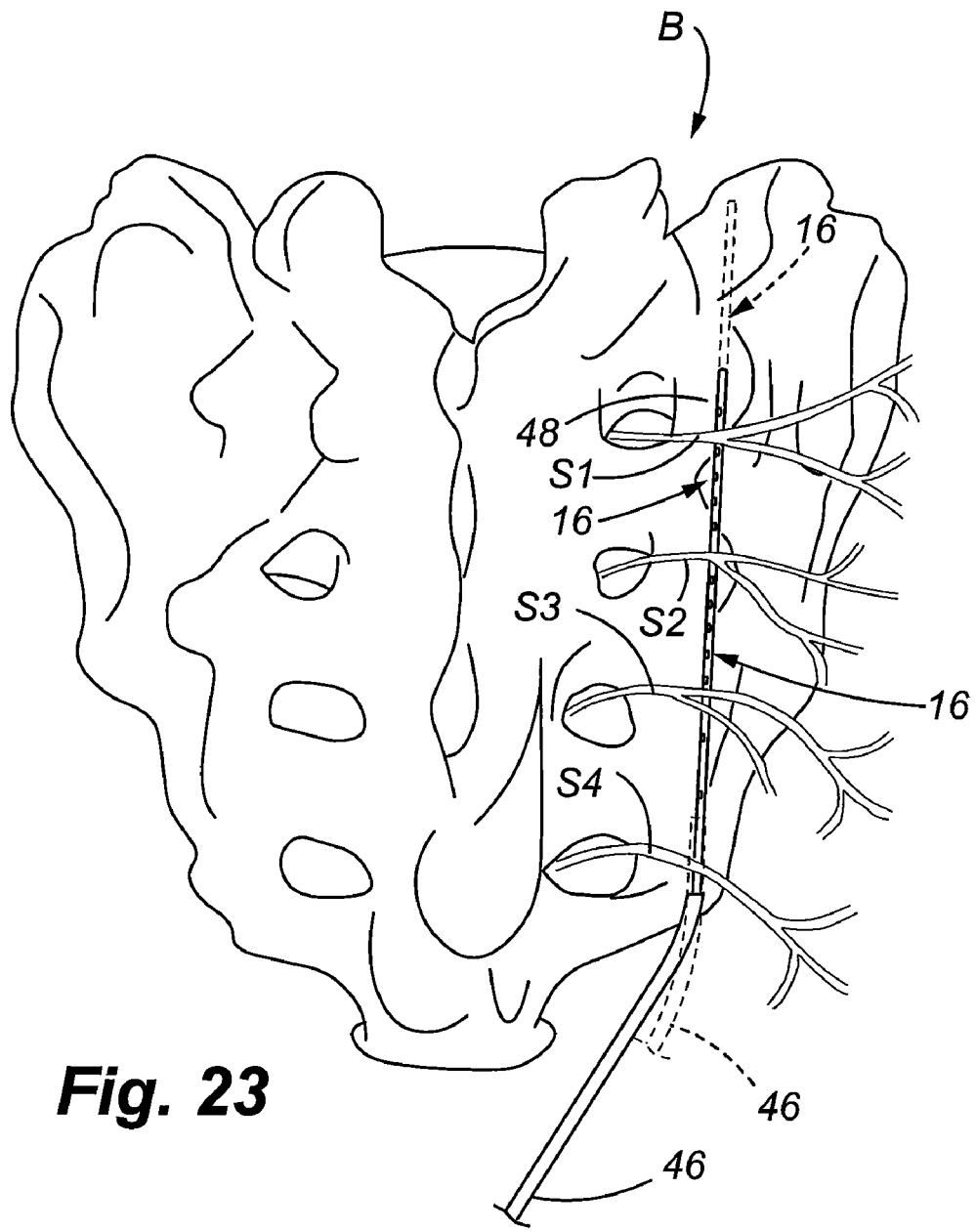
FIG. 23 is another enlarged anterior view of the sacrum bone showing the introducer needle withdrawn a selected length thereby exposing a specific number or group of electrical contacts/electrodes for denervation of selected sacral nerves.

Referring now to FIG. 21, in another aspect of the present invention, a stimulation device may be used to treat SI joint ailments. FIG. 21 specifically illustrates a posterior view of the sacroiliac region with an introducer needle positioned for insertion along the sacroiliac region to a targeted area adjacent the SI joint J. Referring also to FIG. 22, an enlarged posterior view of the sacrum bone B is shown wherein the introducer needle 46 has been fully inserted. In accordance with a method of the present invention for treatment of the SI joint, the introducer needle 46 is first inserted through the skin below and slightly medial to the inferior aspect to the SI joint and directed towards the inferior lateral edge of the sacrum. The introducer needle 46 is advanced to contact the dorsal aspect of the sacrum at the posterolateral edge. As shown, the needle 46 may have a slight curvature near the distal end thereof, shown as curve or bend 48, and the curvature of the bend 48 is then utilized to advance the needle lateral to the sacral foramen and medial to the dorsal aspect of the SI joint. In another needle configuration (not shown) the distal tip can have a shaper bend and the needle have a continuous curve along all or part of its length to further facilitate positioning along, and parallel to the sacral curvature. The needle 46 remains in contact with the periosteum along the entire curvature of the sacrum. The needle tip ultimately advances to the superior edge of the sacrum lateral to the sacral foramen and medial to the SI joint. Appropriate positioning of the introducing needle is confirmed preferably both on Anteroposterior (AP) as well as lateral views. The stimulation lead 16 is then inserted through the introducer needle 46 until reaching the distal tip 48 of the introducer needle. The stimulation lead 16 is held in place by maintaining pressure on the lead. Referring now to FIG. 23, the introducer needle 16 is withdrawn along a selected length of the stimulation lead 46 to expose the active number of electrodes 22 necessary to denervate the sacral nerve innervation to the SI joint. The dotted lines shown in FIG. 23 for lead 16 represent the initial position of the lead after the needle 46 is withdrawn. After the lead 16 is exposed, local anesthetic and/or neurolytic agents and/or proliferant agents such as, but not limited to, phenol or alcohol, or Dextrose respectively could be injected through one or more of the infusion ports. The electrodes 22 may then be activated to ablate the surrounding neural tissue. The dotted lines for needle 46 in FIG. 23 represent the position of the needle after it has been withdrawn and the lead is ready for activation. The solid lines in FIG. 23 represent the next position of the lead 16 and needle 46 wherein both have been further withdrawn for purposes of conducting another activation to further denervate tissue, such as a circumstance when the initial ablation did not effectively cover the desired area of tissue.

With respect to the specific construction of the stimulation lead for use in a method of treating the SI joint, it may be constructed in the same manner as disclosed with respect to the prior description for treatment of a disc. More specifically, a stimulation lead may be selected having the most desirable arrangement of electrodes for the most optimal denervation of the targeted neural tissues.

The sacral nerves illustrated in FIG. 23 include the lateral branches S1, S2, S3 and S4. In order to denervate each of the lateral branches, it may be required to sequentially apply energy to the stimulation lead as the introducer needle is repeatedly withdrawn along the path of insertion. Because of the variation of sacral anatomy, successful denervation may require two or more separate needle insertion angles in order to denervate the S1-S4 lateral branches. However, as discussed below with respect to the embodiments having multiple lead elements, it may be possible to avoid such multiple needle insertions. In addition to denervation of the sacral lateral branches, it may also be advantageous to denervate the L5 dorsal ramus as well as the L4 medial branch since there is some innervation to the SI joint from both of these additional nerve structures.

Although the figures show treatment along one side of the sacrum, it shall be understood that the same procedure may be repeated for treatment of the other side of the sacrum, by placement of the introducer needle in a symmetrical fashion on the corresponding opposite or contralateral side of the sacrum. In addition to electrical stimulation, it is also contemplated with respect to the method of treatment of the SI joint to also provide infusion in a combined electrical stimulation and chemical/drug infusion device. For example, infusion of collagen proliferants could be included in the method of treatment by use of a selected device including any one of the above-disclosed embodiments. Infusion of collagen proliferants such as dextrose, growth factors, and other nutrients may accelerate the healing process for some SI joint ailments. Depending upon the diagnosed ailment, infusion alone may be appropriate for the treatment, or in combination with some neural tissue ablation or stimulation. It is also contemplated in the method of the present invention to enhance neurolytic lesion size by infusion of substances such as Phenol, alcohol, and glycerin.

FIG. 24 illustrates yet another preferred embodiment of the present invention. In this embodiment, the stimulation lead has a substantially uniform curvature over a selected length of the stimulation lead. The amount of curvature provides a desired angle for extending the stimulation lead within the targeted area of the body. Additionally, the distal end 20 of the stimulation lead is similar to what is shown in FIGS. 4 and 6, and therefore may have an additional bend that assists the medical practitioner in steering the stimulation lead once it has exited the distal end of the introducer needle 32. This particular shaped stimulation lead may also be advantageous in conducting treatment of the SI joint as discussed above with respect to FIGS. 21-23.

FIG. 25 illustrates the stimulation device of FIG. 24 for purposes of treatment of vertebral structures other than a disc, such as ventral vertebral structures that are to be ablated.

FIG. 26 illustrates yet another preferred embodiment of the present invention wherein the stimulation lead is substantially liner or straight, and a stylet 76 is placed through a central lumen of the stimulation lead. For the embodiment of FIG. 26, the stylet 76 may be used to steer the stimulation lead, and to provide the necessary stiffness to the stimulation lead during emplacement. Once the stimulation lead has been manipulated to the desired position, the stylet 76 can be removed while keeping the stimulation lead stationary. Then, the desired electrical stimulation procedure can be conducted along with any desired infusion.

Figure 27:
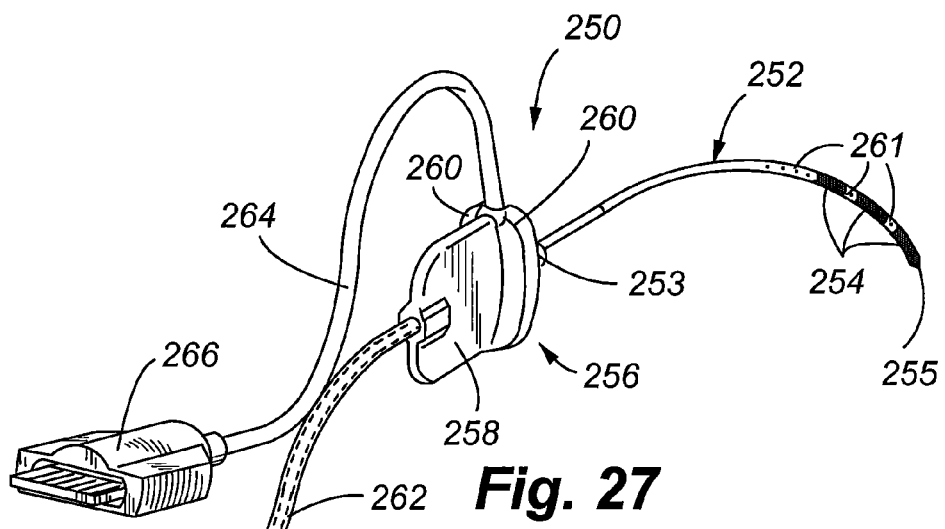
FIG. 27 illustrates yet another preferred embodiment of the present invention in the form of a stimulation lead that can be either disposable, or reusable when used with a disposal outer sheath.
Figure 28:
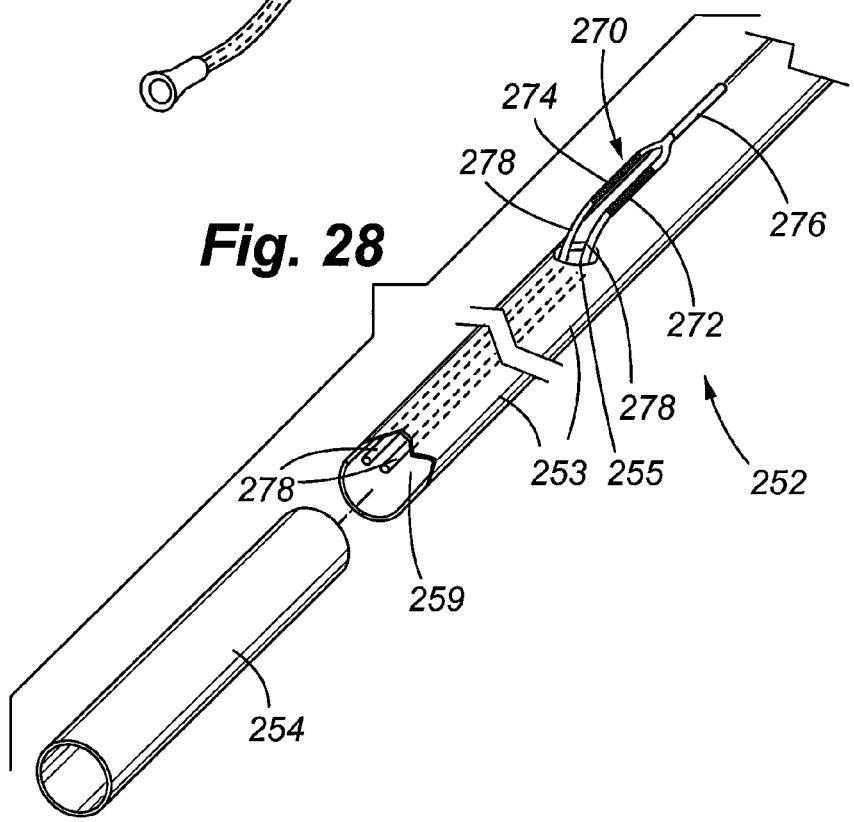
FIG. 28 is an enlarged fragmentary perspective view of the body of the stimulation lead of FIG. 27 illustrating details thereof.

Now referring to FIGS. 27 and 28, a stimulation lead 250 is illustrated that can either be used as a reusable stimulation lead placed within an outer sheath (see e.g., FIG. 32), or the stimulation lead 250 may be used by itself as a disposable stimulation lead. As shown, the stimulation lead 250 includes a stimulation body 252, and a plurality of electrodes 254 that are located at the distal end of the body 252. The tip 255 may be blunt, or may include a trocar, Quincke, Touhy, or other penetrating/cutting type tip if the stimulation lead is to be forced through fairly dense tissue. A handle 256 is provided wherein the handle includes a central web 258, and a pair of transverse flanges 260 that extend substantially perpendicular to the central web 258. With the handle 256, the combination of the transverse flanges 260 and the web 258 allow the handle to be manipulated to rotate, twist, push, or pull the body 252 to precisely locate the stimulation lead. If it is desired for the device to be able to provide infusion, a fluid line 262 can be provided that communicates with a central lumen 259 of the stimulation lead such that infusion may take place through selectively located infusion ports 261. A cable 264 and multi-pin connector 266 are provided to power the electrodes 254.

Referring specifically to FIG. 28, an enlarged fragmentary perspective view is provided illustrating how the electrodes 254 may be secured to a non-conductive sheath 253. The non-conductive sheath and electrodes collectively make up the body. The non-conductive sheath 253 may be made of material such as plastic. An opening 255 may be made in the sheath to receive wires 278 which in turn are connected to conductors 272 and 274 forming a thermocouple. Junction 276 terminates the opposite ends of the pair of wires 278. The electrode 254 is in the form of a tubular member that fits over the sheath 253 and is secured to the sheath 253 by an appropriate adhesive, crimping, or other techniques. The wires 278 and thermocouple contact the electrode 254. The connection of the electrodes 254 over the sheath 253 is preferably watertight such that the central lumen 259 is shielded from the external environment. Wires 278 conduct power to the electrodes to include RF signals, as well as serving as conductors for measurement of electrical potential between the thermocouple elements 272 and 274.

Figure 31:
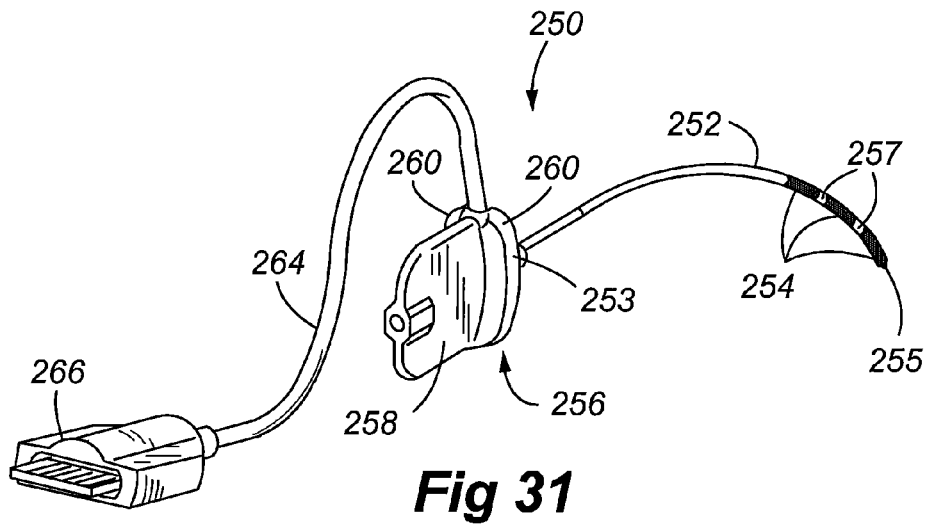
FIG. 31 is a perspective view of the stimulation lead similar to the stimulation lead of FIG. 27, however, the stimulation lead of FIG. 31 being especially adapted as a reusable stimulation lead with no infusion capability.
Figure 32:
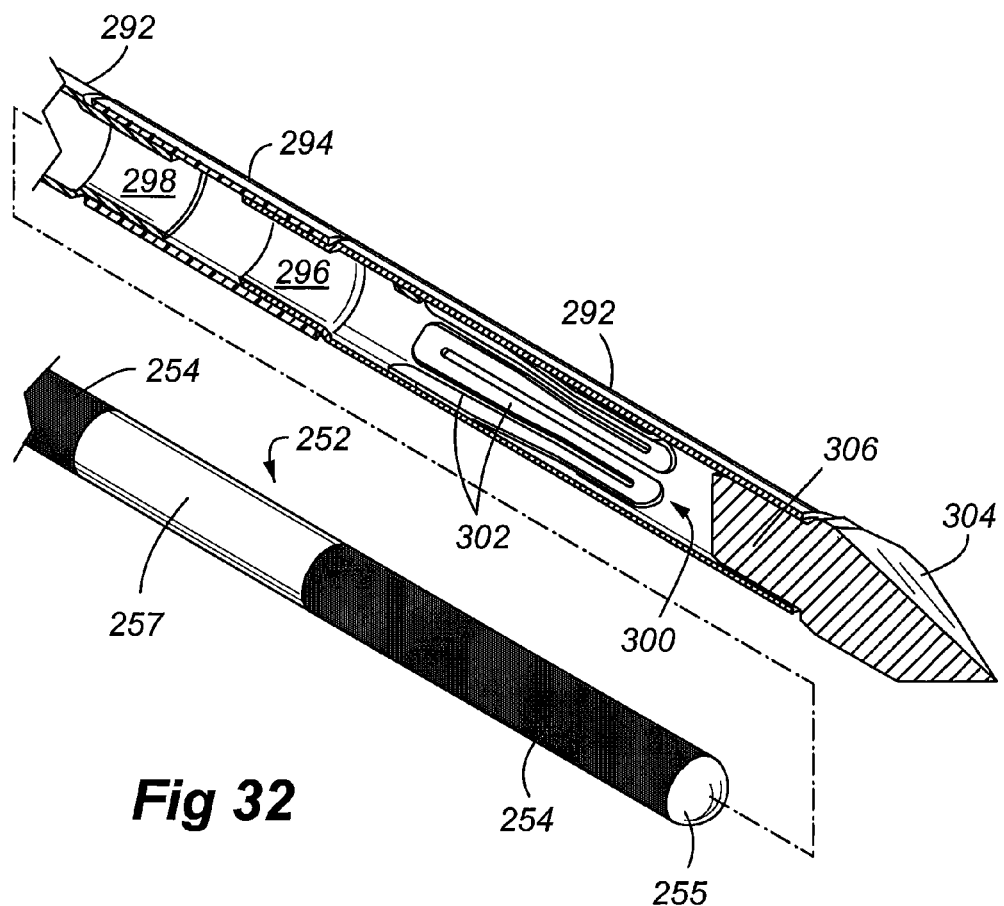
FIG. 32 is an enlarged fragmentary perspective cross-section of the sheath of FIG. 30 and the body of the stimulation lead of FIG. 31 illustrating how the lead is inserted within the sheath.

FIGS. 29 and 30 illustrate a disposable sheath 290 that can be used in conjunction with a reusable stimulation lead 250 of FIG. 27. As shown in FIG. 29, the disposable sheath 290 may include a plurality of conductive sections 292 which act as electrodes when placed in electrical contact with the electrodes of the reusable stimulation lead. Insulated non-conductive connectors 294 interconnect each of the electrodes 292. One simple method of connection is to provide smaller diameter flanges for the conductive sections, shown as flanges 296 and 298, and then press fit the sections together. Within each conductive section 292 is a spring finger conductor 300. The conductors are placed within each of the conductive sections 292 such that the traversing pattern of fingers 302 presses against the interior surface of the conductive sections 292. A desired shaped tip 304 may be provided for the sheath, shown in FIG. 29 as a trocar type tip having a tapered sharpened end 304, and a base 306 that is received in the most distal end of the conductive section 292. Referring to FIG. 31, the reusable stimulation lead 250 shown there is the same as stimulation lead 250 shown in FIG. 8, except that the infusion line 262 has been eliminated. Referring to FIG. 32, the body 252 of the stimulation lead 250 is inserted within the disposable sheath 290 so that the electrodes 254 of the stimulation lead align with the conductive sections 292, while the non-conductive sections 257 of the stimulation lead 250 align with the non-conductive sections 294 of the sheath. As the body 252 is placed within the sheath 290, the fingers 302 make frictional contact with the electrodes 254; the fingers 302 also being in contact with the conductive sections 292 creates an electrical pathway such that energizing selected one or all of the electrodes 254 results in energizing the corresponding conductive sections 292. With respect to measuring temperature at the conductive sections 292, temperature-sensing elements such as a thermocouple may be incorporated in the stimulation lead 250 as disclosed above in FIG. 28. Thus, the temperature of the conductive sections 292 may be measured since by conduction, thermal contact is maintained between the active areas of the stimulation lead and the conductive areas on the external sheath. One clear advantage of providing a disposable sheath 290 is that the sheath may be sized, shaped and otherwise designed for conducting a desired procedure. Use of a reusable stimulation lead lowers the cost of the procedure since the entire assembly does not have to be replaced in the next procedure; only the disposable sheath.

Figure 33:
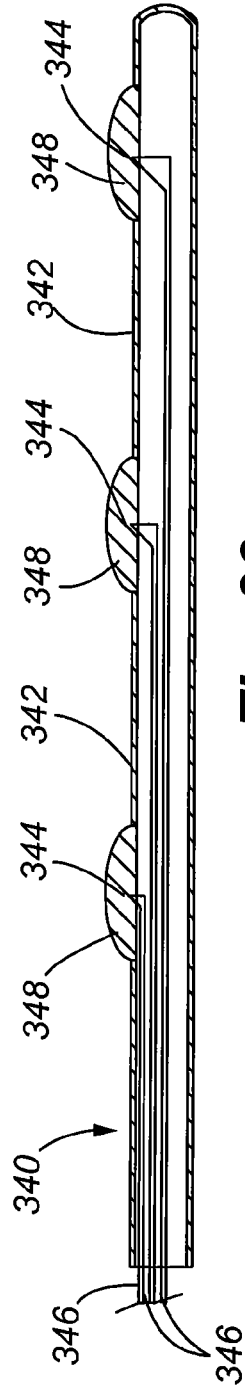
FIG. 33 illustrates a cross-section of yet another reusable stimulation lead especially adapted for use with a disposable sheath.

Referring to FIG. 33, an alternate type of reusable stimulation lead 340 is illustrated. FIG. 33 only illustrates the body 342 of the stimulation lead, it being understood that this embodiment may also include a handle, cable, an electrical connector, the same as shown in FIG. 31. For the stimulation lead 340, a plurality of flexible electrical conductive pods 348 may be disposed at selected locations on the body 342. In the example of FIG. 33, there are three linearly aligned conductive pods; however it should be understood that each of the pods 348 can be selectively placed such that they are spaced not only longitudinally along the length of the stimulation lead, but also circumferentially around the stimulation lead. Electrical energy is provided to each of the conductive pods 348 by pairs of wire conductors 346 that traverse through a central lumen of the body 342. Each pair of wires may include a thermocouple 344 that is placed in the electrical contact with conductive pods 348. As with the other embodiments, wire pairs 346 may be used to provide RF signals, as well as conductors for measuring differences of electrical potential at the thermocouples 344. The stimulation lead 340 may then be inserted within a disposable sheath, such as the one discussed above with respect to FIGS. 29 and 30, or with an alternate sheath assembly discussed below with respect to FIGS. 34-36.

Figure 34:
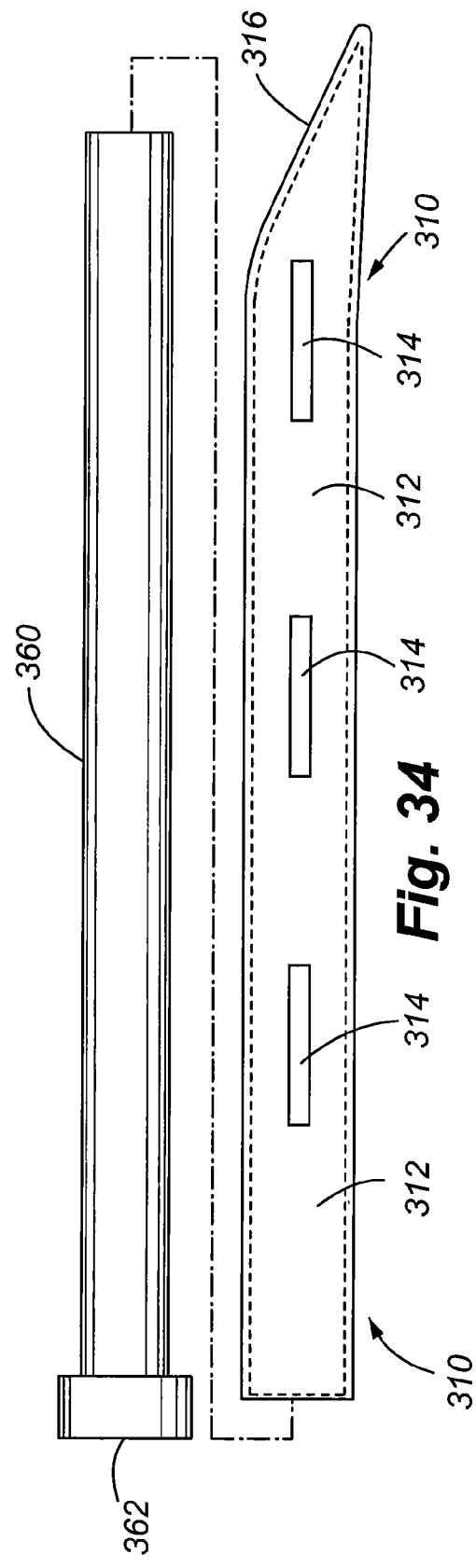
FIG. 34 illustrates a component of another type of disposable sheath along with a stiffening opturator.

Referring to FIG. 34, this alternative sheath embodiment 310 is characterized by a very flexible body 312 having a plurality of slots or openings 314 formed therein. A distal end of the body 312 includes a tip 316. The tip can be blunt or sharp, depending upon the intended use. Referring to FIG. 35, electrodes 318 are cylindrical shaped sections that are slipped over the body 312, in the same manner as disclosed with respect to FIG. 28. However, in the case of FIG. 35, a bracket 320 is used to interconnect the electrodes from the reusable stimulation lead with the electrodes 318 formed on the sheath. As shown, the bracket 320 may include a pair of traverse flanges 322, sidewalls 326, and base 328. Accordingly, a channel 324 is formed between the sidewalls and base. The bracket 320 is placed in a corresponding slot 314 such that the flanges 322 rest on the outer surface of the body 312. When the electrode 318 is slipped over the body 312, the electrode 318 is aligned such that it covers the bracket 320. The electrode 318 is secured to the body 312 as by crimping, or by spot welding. Adhesive may also be used to ensure there is a liquid tight seal. In FIG. 36, the thickness of the electrode 318 has been accentuated to enable understanding of how the electrode 318 is secured. However, it is preferable to provide a substantially smooth and continuous outer surface for the body 312 and electrodes 318, or at least a minimal protrusion of the electrode 318 above the outer surface of the body 312. One technique to ensure a smooth outer surface would be to form a channel in the body 312 to accept the electrode 318. When the reusable stimulation lead is placed within the central lumen of the sheath, the electrodes of the reusable stimulation lead make contact with the respective bases 328 of the brackets 320, thereby also energizing the respective electrodes 318. As shown in the cross-section of FIG. 36, the three linearly aligned electrical conductive pods 348 make contact with the three linearly aligned brackets 320.

Referring back to FIG. 34, an opturator 360 may be used when first emplacing the disposable sheath in a position where treatment is to be applied. Because of the very thin body 312, interior support of the opturator is necessary prior to insertion of the reusable stimulation lead. The opturator may have a standard end connection or flange 362 enabling it to be controlled in placing the disposable sheath 310.

FIG. 37 illustrates another configuration of the embodiment of FIGS. 34-36 wherein an alternate shaped bracket 350 is provided. This bracket 350 includes a curved base 352, and a pair of opposing end flanges 354 that make contact with the outer surface of the body 312. The electrode 318 is slipped over the body 314, and the electrode 318 covers the bracket. The conductive pod 348 makes contact with the curved base when the stimulation lead 340 is placed within the sheath. Because of the curved shape of the bracket 350, some resiliency is present when the pod 348 makes contact thereby ensuring a good electrical connection.

FIGS. 38 and 39 illustrate yet another preferred embodiment of the present invention in the form of a disposable sheath and reusable inner stimulation lead or probe. Beginning first with FIG. 38, a reusable probe 400 is shown having a plurality of spaced active areas or electrodes 402, a distal end 406, and insulated, non-conductive sections 404 located between the electrodes 402. The disposable sheath 410 of the present invention is shown fully manufactured in FIG. 39. FIG. 38 illustrates the disposable sheath during manufacturing wherein a plurality of electrode assemblies 412 are selectively spaced from one another along an inner mandrel 418. A sharp metallic or plastic tip, such as a trocar 420, is secured to a distal end of the mandrel 418. Each of the electrode assemblies 412 include a plurality of electrode elements 414 that extend longitudinally along a length of the corresponding electrode assembly, and the elements 414 are spaced from one another circumferentially around the electrode assembly. An electrode sleeve 416 serves as a base to secure the electrode elements 414. The electrode assemblies to include the electrode elements and sleeves are made of a desired conductive material. The electrode elements 414 are shaped such that they extend radially away from the longitudinal axis of the mandrel in an arc shape. Therefore, the electrode elements 414 extend a radial height above the outer surface of the respective electrode sleeves 416. A non-conductive thermoplastic material is then applied over the mandrel 418, such as by molding or by spray deposition wherein a sheath body 422 is formed. The electrode sleeves 416 and some parts of the electrode elements 414 are embedded within the applied sheath material. Accordingly, the electrode members have at least an outer most radial surface that remains exposed. The particular sheath body material may be selected to provide the desired flexibility or stiffness for the disposable sheath. Additionally, the sheath material can be applied at a desired thickness to account for the amount of the electrode elements 414 to be exposed. The mandrel 418 is then removed from within the now formed disposable sheath wherein the cylindrical inner surfaces of the electrode sleeves 416 are exposed within the interior of the sheath. When the stimulation lead 400 is placed within the disposable sheath, the electrodes 402 align with the respective electrode sleeves 416, thereby achieving electrical contact between each of the electrode assemblies 412 and respective electrodes 402. The device then may be used to conduct a desired procedure wherein the exposed portions of the electrode elements 414 are used to deliver energy to the patient. In the embodiment of FIG. 39, the sheath body material may extend over a base or proximal portion of the trocar tip 420 such that a good seal is achieved and thereby completely isolating the stimulation lead within the disposable sheath.

Now referring to FIGS. 40 and 41, another embodiment is illustrated with respect to a disposable sheath that may be used with a stimulation lead. FIG. 40 illustrates a stimulation lead, such as stimulation lead 400, that is placed within a disposable perforated sheath 430. The perforated sheath 430 includes a plurality of perforated sections 432, each section having a plurality of openings that therefore expose the respective electrodes of the stimulation lead. More specifically, with the stimulation lead 400 of FIG. 40, three electrodes are illustrated, namely a most distal electrode 450, and two spaced proximal electrodes 446 and 448. The electrodes 446, 448, and 450 align with respective perforated sections 432 of the sheath. Preferably, the sheath 430 is made of a non-conductive material, but the thickness of the material is very thin such that when the stimulation lead is placed within a patient, tissue of the patient is allowed to penetrate the perforations 432 and therefore come into contact with the stimulation lead. With the embodiment of FIG. 40, the sheath provides protection to the stimulation lead, thereby increasing its life. The stimulation lead must be resterilized after use, but the disposable sheath provides a protective jacket without substantially inhibiting the ability of the electrodes to deliver energy to targeted tissue.

FIG. 41 illustrates yet another disposable sheath 440 of the present invention. The disposable sheath 440 includes a plurality of insulated or non-conductive sections 442, and at least one conductive area or section 444. The conductive section 444 also includes a plurality of openings formed therein, therefore making the conductive section 444 appearing as if it is perforated. One specific use for the disposable sheath 440 shown in FIG. 41 is to alter the electrode pattern of the inner stimulation lead 400. In the case of FIG. 1, the longitudinal length of the conductive area 444 causes it to bridge between the underlying electrodes 446, 448, and 450 thereby creating one continuous and larger sized electrode that will result in creation of a different ablative pattern once the stimulation lead is energized. Taking this general concept further, the disposable sheath 440 may have a desired configuration of insulated areas and conductive areas that alter the basic electrode pattern of the underlying stimulation lead. The benefits of this embodiment also include some protection for the inner stimulation lead.

FIGS. 42-44 illustrate yet further embodiments of the present invention, showing in more particular detail various construction techniques for forming stimulation leads that have a selected pattern of electrodes and non-conductive sections. Referring first to FIG. 42, the stimulation lead 460 is shown in the form of a segmented probe having a plurality of electrode sections 462 spaced between respective non-conductive sections 464. Electrical continuity can be achieved between the various electrode sections 462 by the use of conductive extensions 466 that are inserted within the openings formed through the adjacent non-conductive sections 464. The stimulation lead 460 in FIG. 42 has a distal stimulation lead 462 incorporating a trocar tip 474. The actual configuration of the electrode elements 463 of each section 464 can incorporate various constructions to include conductive wires wound in a pattern, solid electrical members, and others. The proximal ends 469 of each conductive extension 466 are inserted into distal ends of the adjacent non-conductive sections 464. The distal ends 468 of the electrode extensions 460 are inserted in the opposite, proximal ends of the adjacent non-conductive sections 464. The abutting ends 468 and 469 within each non-conductive sections make contact with one another, thereby providing electrical continuity between the electrodes. The diameter of the conductive extensions 466 may be such that a friction fit is achieved between the conductive and non-conductive sections. An approved epoxy may also be used to ensure that the sections do not separate from one another. It is also contemplated that the conductive extensions 466 may include a plurality of conductive pins (not shown) that selectively mate with corresponding pins (not shown) of other conductive extensions, thereby providing the capability to alter or change the electrical connections between the respective electrodes. For example, if it is desired to operate the electrodes in a mono-polar configuration, an RF generator driving the stimulation lead can have settings that cause leads to be activated only in the mono-polar configuration, whereby the electrical pins between the conductive sections conduct RF power signals and a grounding pad is used. Further for example, if it is desired to operate the electrodes in some type of bipolar configuration, the electrical pins would conduct RF power signals in a different manner between the electrodes as controlled by the RF generator.

FIG. 43 illustrates a stimulation lead similar to the one described above with respect to FIG. 42, except that the stimulation lead in FIG. 43 includes a plurality of splines 476 that are used to ensure a tight connection between the conductive and non-conductive sections. As shown, the splines 476 are secured to the conductive extensions 466 and have free ends that extend at a radial angle away from the longitudinal axis of the stimulation lead. The free ends of the splines 476 may be sharpened or pointed. When a conductive extension is inserted within its adjacent non-conductive section, the free ends of the splines make contact with the interior wall of the non-conductive section, thereby providing frictional resistance against pullout.

FIG. 44 illustrates yet another modification to the stimulation lead illustrated in FIG. 42. In FIG. 44, the conductive and non-conductive sections may be secured to one another by incorporation of a key/keyway arrangement. More specifically, the conductive extensions 466 each have a key 470 that protrudes radially, and is received in keyways 472 which are formed at the ends of the adjacent non-conductive sections 464. The shape of each keyway 472 may be such that each key 470 is prevented from removal from within the corresponding keyway. In the example of FIG. 44, the keyways 472 are L-shaped allowing the keys 470 to lock in the keyways 472 by rotating the keys to reside in the transverse slots of the keyways. FIGS. 45 and 46 illustrate yet additional construction details for the manufacture of a stimulation lead in accordance with another modification to the present invention. As shown in FIG. 45, the conductive extensions are threaded extensions 480 that are received in internally threaded openings 478 of the non-conductive sections. The abutting distal and proximal ends of the conductive extensions 480 within each non-conductive section make contact with one another to thereby achieve electrical continuity between the electrodes in the same manner as described above in FIG. 42. Referring to FIG. 46, yet another construction option includes the use of interconnecting pegs 482 that interconnect the respective conductive and non-conductive sections. The abutting distal and proximal ends of the pegs 482 within each non-conductive section make contact with one another to thereby achieve electrical continuity between the electrodes also in the same manner as described above in FIG. 42 with respect to the conductive extensions. The construction details for the stimulation lead shown in FIGS. 42-46 allows for creation of a stimulation lead having conductive and non-conductive sections that are mechanically locked to one another and also provides a designer with many options in terms of selecting the length and size of the conductive and non-conductive sections to be used.

FIG. 47 is an enlarged view of one particular construction for an electrode 490. In this construction, the electrode is simply a conductor such as a wire 492 that forms a helical pattern on the stimulation lead. By changing the helical pattern of the wire, and/or changing the wire gauge, the electrical characteristics of the electrode may be easily altered and therefore, making possible the use of the stimulation lead with very different types of electro-surgical procedures.

Figure 48:
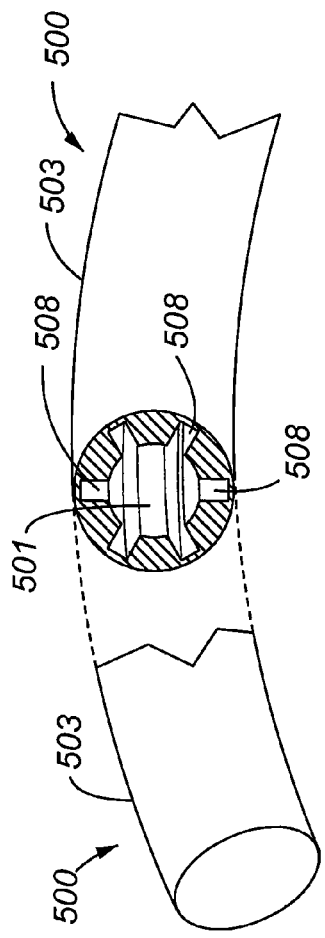
FIG. 48 is a fragmentary perspective cross-sectional view illustrating one step or phase in the manufacture of a disposable sheath usable with an electrical stimulation device.
Figure 49:
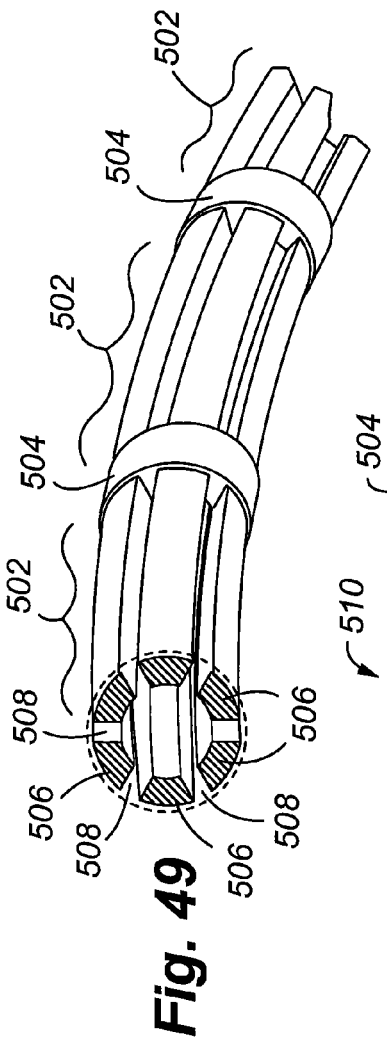
FIG. 49 is a perspective view of the disposable sheath of FIG. 48 illustrating the disposable sheath in yet another step in the manufacturing process.

Now referring to FIGS. 48-51, in yet another embodiment of the present invention, a disposal sheath 500 is illustrated. Referring first to FIG. 48, the disposal sheath 500 is shown in a first manufacturing step wherein a tubular piece of material or blank is provided having a molded interior defined by a central lumen or opening 501 extending therethrough. A plurality of circumferentially spaced gaps 508 extend radially away from the central or longitudinal axis defined by the lumen 501. In the example of FIG. 48, there are six evenly spaced gaps 508. Now referring to FIG. 49, the tubular piece of material is milled or cut to form the configuration shown wherein selected portions of the outer surface 503 of the material are removed thereby forming a plurality of legs 506 that are spaced from one another by the gaps 508. Selected portions of the outer surface 503 are not removed and remain thus forming insulating spacers 504 that serve as non-conductive sections of the disposable sheath. Now referring to FIGS. 50 and 51, conductive material is applied over the milled or cut sections 502 thus forming respective electrodes 510. Each of the electrodes 510 includes an outer peripheral conductive portion 512 as well as a plurality of radial conductors 514 which fill the gaps 508. In the preferred embodiment shown in FIGS. 50 and 51, it is noted that the radial conductors 514 terminate at interior edges 515, and which complete a substantially circular lumen 501.

Figure 50:
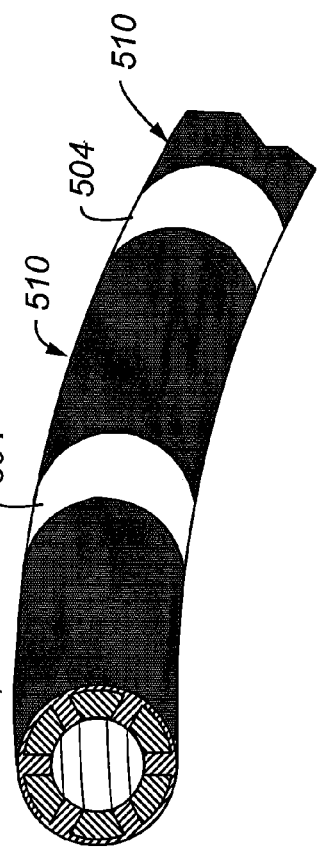
FIG. 50 is a perspective view of the disposable sheath of FIGS. 48 and 49, showing the sheath as fully manufactured.
Figure 51:
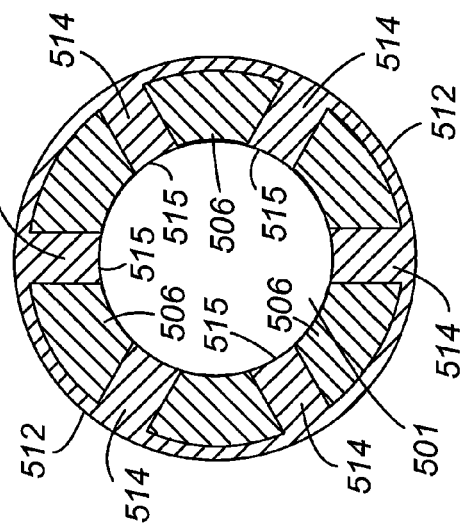
FIG. 51 is an end view of the disposable sheath of FIGS. 48-50, illustrating various features of the sheath to include how the electrically conductive sections are arranged with respect to non-conductive portions of the sheath.

Examples of conductive material that may be used to form the electrodes include conductive resins that are molded to form the electrodes in the shape as shown in FIGS. 50 and 51. Another material in which to form the electrodes 510 includes metallic cylindrical bands with integral radial conductors that are sized and shaped to fit the particular milled or cut pattern of legs 506 and gaps 508. With the disposal sheath shown in this embodiment, a stimulation lead, such as the stimulation lead 400, may be placed through the lumen 501 where the electrodes on the stimulation lead align with the radial conductors 514 exposed within the lumen. The distal end of the sheath may be sealed thereby allowing the reusable inner stimulation lead to be reused without the need for re-sterilization, and may also include a sharpened distal tip, such as a trocar point, milled from the blank. The sheath 500 may be formed in a desired curved shape and may be made relatively stiff or have some flexibility, depending upon the types of material used for the blank and the electrodes. Since each of the conductive areas/electrodes on the sheath are isolated from one another electrically, the same activation functionality provided for the stimulation lead can be maintained with use of the sheath.

Figures 52, 53:
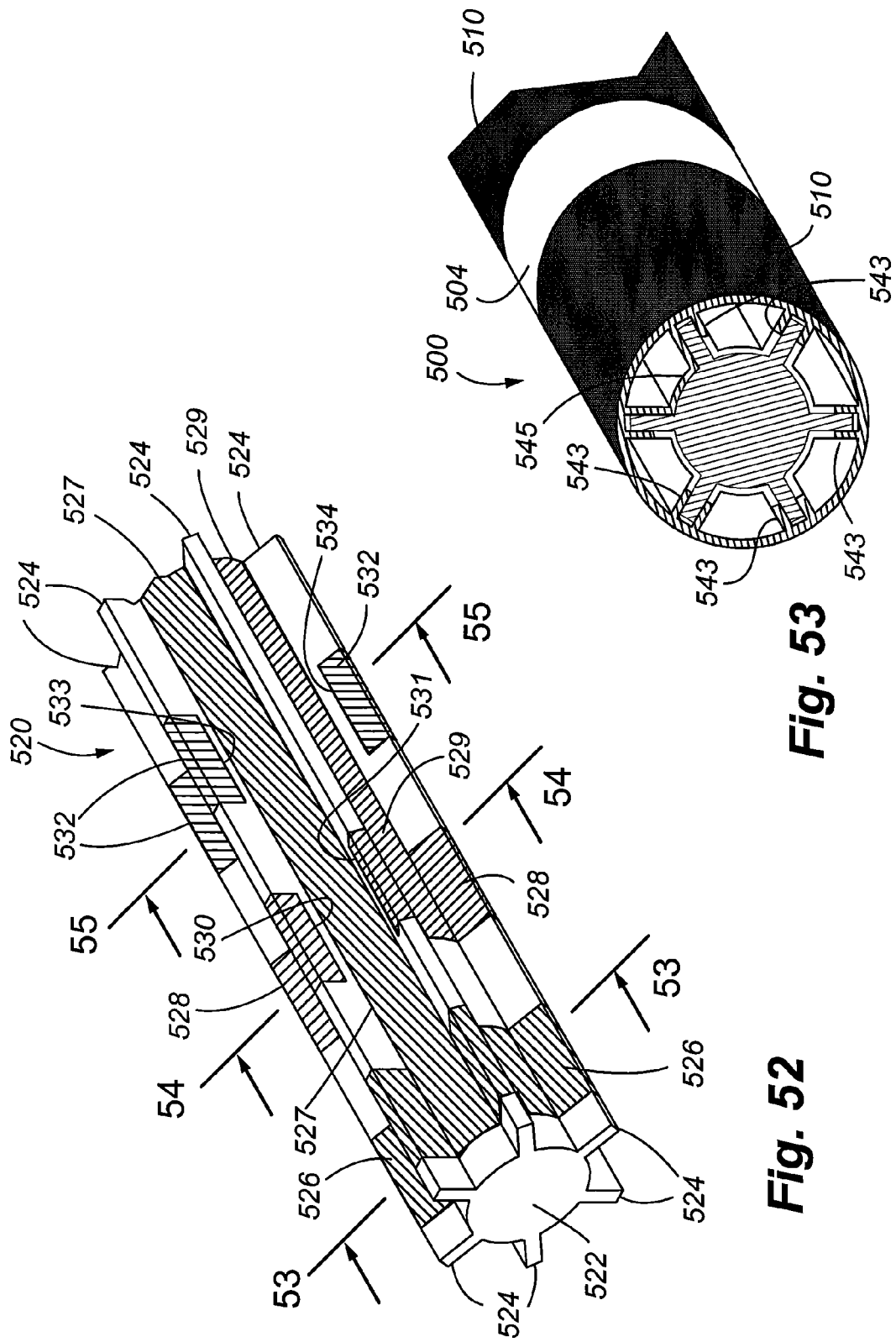
FIG. 52 is a perspective view of a reusable-keyed stimulation lead or probe usable with a disposable sheath.
FIGS. 53-55 are cross-sections taken along respective lines 53-53, 54-54, and 55-55 of FIG. 52 illustrating a disposable sheath used with the keyed stimulation lead of FIG. 52.
Figure 55:
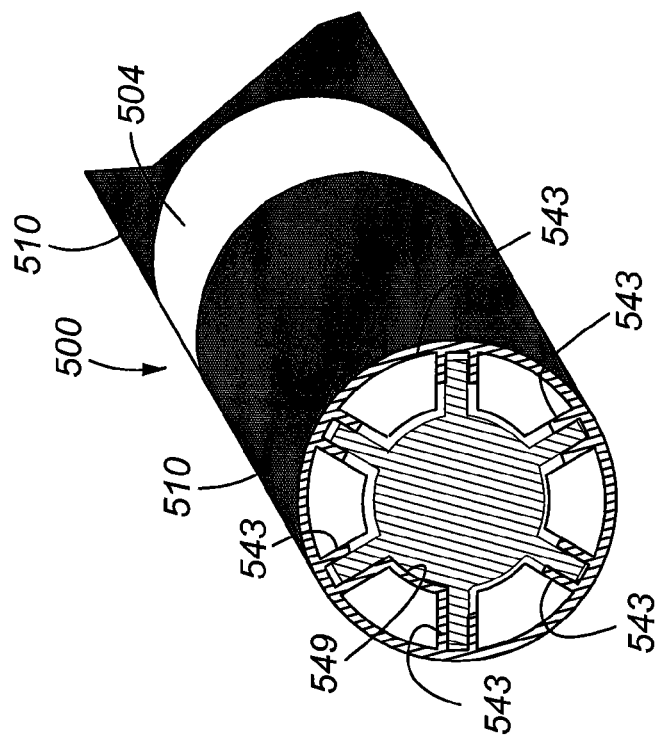
Figure 54:
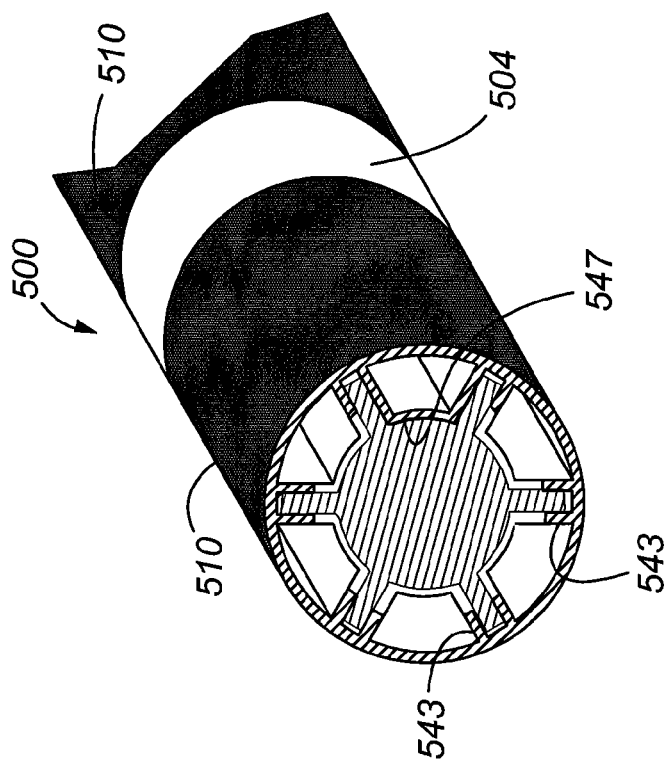

FIG. 52 illustrates a reusable-keyed probe or stimulation lead 520 that is used with the outer sheath 500 illustrated in FIGS. 53-55. The reusable-keyed probe 520 is characterized by a central portion 522 having a substantially cylindrical shape. A plurality of circumferentially spaced keys 524 extend radially away from the central portion 522. A plurality of conductive rings and conductive extensions are incorporated on the probe. More specifically, a most distal conductive ring or strip 526 extends continually over the keys and central portion. A conductive extension 527 is electrically connected to the conductive ring 526 and extends along a channel between respective adjacent pairs of keys 524. Another conductive ring or strip 528 is spaced proximally from conductive ring 526. Conductive ring/strip 528 has its own corresponding conductive extension 529, which extends proximally within another channel between a corresponding pair of keys 524. Yet another conductive ring or strip 532 is spaced proximally from the ring/strip 528 and the conductive ring/strip 532 has its own proximally extending conductive extension (not shown) which extends along another channel located between a corresponding pair of keys 524. Referring to the conductive extension 527, it is seen that this conductive extension does not make electrical contact with any of the other conductive rings or conductive extensions. The conductive ring/section 528 terminates at ends 530 and 531 such that there is no electrical contact between conductive ring 528 and conductive extension 527. Similarly, as the conductive extension 527 extends further proximally along the keyed probe, it is shown that the conductive ring/strip 532 has respective ends 533 and 534 that do not allow the conductive ring/strip 532 to contact the conductive extension 527. It is also noted in FIG. 52 that the conductive extension 529 is not contacted by any other conductive ring/strip or conductive extension, noting that one end 534 of the conductive ring/strip 532 terminates at a spaced distance from the conductive extension 529. Thus, with the keyed probe as shown in FIG. 52, a plurality of longitudinally spaced yet electrically isolated conductive rings may be provided along the length of the keyed probe.

Now referring to FIGS. 53-55, the keyed probe 520 is illustrated with respect to a disposable sheath 500. The sheath 500 shown in FIGS. 53-55 is the same as shown in FIGS. 48-51, with the exception that the radial conductors 514 are replaced with radial conductors 543 that extend into the respective gaps 508, but do not completely fill the gaps and therefore create a channel to receive the corresponding keys 524. The radial conductors 543 preferably extend along only a portion of the length of the corresponding gap, with the exception of conductive portions which are used to make contact with corresponding conductive extensions of the key probe, as discussed further below. The radial conductors 543 therefore only cover an outer radial portion of the keys 524. As shown in the cross-section of FIG. 53, the arrangement of the most distal conductive section 510 is such that an inner peripheral conductive portion 545 of this conductive section 510 makes intimate contact with the conductive extension 527, thereby allowing energy to be delivered to the patient along the circumferentially extending conductive section 510, and wherein the energy delivered to the conductive section 510 is electrically isolated from the other electrodes/conductive sections 510 and thus may be independently controlled.

Referring to FIG. 54, this cross-section taken along line 54-54 FIG. 52 shows that the conductive ring/strip 528 makes contact with the intermediate or middle conductive section 510 and further wherein conductive portion 547 aligns with conductive extension 529 such that energy may be conducted from conductive extension 529 throughout this conductive section 510. Since the intermediate conductive section 510 and conductive strip 528 are also electrically isolated from the other conductors and conductive sections, this electrode 510 may be independently controlled. Now referring to FIG. 55, this cross-section is taken along line 55-55 of FIG. 52 showing that conductive ring/strip 532 makes electrical contact with the proximal conductive section 510. Conductive portion 549 makes intimate contact with the corresponding conductive extension (not shown) of ring/strip 532 such that this proximal conductive section 510 can also be independently controlled.

Although the keyed probe 520 may be reusable since it is fully sealed within the sheath 500, it is also contemplated that both the keyed probe 520 and sheath 500 may be considered disposable wherein the probe 520 during manufacturing is secured within the sheath.

Depending upon the material used for the sheath 500 and probe 520, it is contemplated that the sheath/probe combination may be emplaced with or without the need for an introducer needle.

There are a number of advantages to the keyed probe of FIG. 52 used in conjunction with the external sheath 510 shown in FIGS. 53-55. First, it is noted that because of the keyed arrangement of the keyed probe 520, there is no possibility of shifting which might otherwise alter the orientation of the various electrically conductive areas. Thus, the keyed arrangement ensures that the probe is structurally stable with respect to the sheath and targeted areas of tissue will be reliably treated since there is no possibility that the sheath will shift with respect to the inner probe. As noted, with the particular arrangement of the conductive extensions and the conductive rings/strips, conductive paths are provided to the electrodes on the sheath, wherein the conductive paths are electrically isolated from one another and therefore, both mono-polar and bipolar ablative lesions can be obtained at various locations and combinations along the length of the probe.

Although the central lumen 501 and the gaps 508 have been illustrated as extending parallel with the longitudinal axis of the sheath 500, it should also be understood that the gaps 508 may extend in a helical configuration and therefore, the keyed probe 520 may also be provided in a helical configuration to match the orientation of the helical gaps 508. This spiraled or rifling configuration may further help to prevent shifting of the keyed probe with respect to the external sheath.

Now referring to FIG. 56, a disposable stimulation lead 600 is illustrated in accordance with yet another preferred embodiment of the present invention. In this embodiment, a handle 602 has a pair of crescent shaped notches or indents 604 that facilitate grasping by the user. A proximal end 608 of the handle 602 incorporates an integral electrical receptacle 618, as shown in FIG. 57. An electrical plug 610 is mateable with the receptacle 618, and as shown in FIG. 57, a desired electrical pin arrangement 616 is adapted for connection to the receptacle 618. Various means may be provided to ensure positive locking of the plug 610 with respect to the handle 602, such as by incorporation of a key 620 in the plug 610, and a keyway 622 incorporated within the proximal end 608 of the handle 602. An electrical cable 612 interconnects the plug 610 with an RF generator 614. A stimulation lead 624 extends from the distal end 606 of the handle 600. The stimulation lead 624 includes a desired arrangement of active areas/electrodes 630 separated by corresponding insulated or non-conductive areas 632. The electrodes 630 are powered by the RF generator 614. Electrical conductors (not shown) extend through the interior of the handle 602 and electrically interconnect the electrodes to the receptacle 618. Optionally, infusion ports 633 may be selectively spaced along the stimulation lead and a central lumen may be used to convey infusion material to the ports. Preferably, the shape of the stimulation lead 624 resembles the shape of the stimulation lead illustrated in FIG. 24 wherein a slight curvature is incorporated substantially along the length of the stimulation lead. Additionally, the distal tip or portion of the lead may have a bend that does not follow the curvature of the rest of the stimulation lead, however this bend is co-planar with the rest of the stimulation lead. This bend can be slight or more pronounced depending upon how the practitioner wishes to emplace the lead in its path to the targeted area. With respect to temperature-sensing elements such as thermocouples, RTDs, or other temperature sensing elements, the embodiment of FIG. 56 may incorporate temperature-sensing elements, and FIG. 28 provides one example by which a thermocouple may be incorporated in the embodiment of FIG. 56.

In addition to the method of treating the SI joint as explained above with respect to FIGS. 21-23, in yet a further embodiment of the method of the present invention, the stimulation lead 600 of FIG. 56 can also be used with respect to the method of treating the SI joint as illustrated in FIG. 58. In this method, the location of the stimulation lead is shifted as compared to the location of the probe shown in FIG. 21. The position of the probe in this method creates a lesion of the lateral branches of the nerves as the lateral branches converge as a mesh adjacent the dorsal joint, within the enclosed spaced defined between the iliac crest/ilium above, the SI joint laterally, and the sacrum below. More specifically, the stimulation lead 624 is inserted through the skin at the same inferiomedial position to the targeted SI joint, however the stimulation lead is not placed just lateral to the foramen but is placed more laterally to lie captured under the iliac crest/ilium and in contact with the sacrum, on or directly medial to the dorsal SI joint. Accordingly, the lateral branches at their origin as they extend from the foramen are not lesioned, but rather, the lateral branches are lesioned in the defined enclosed space. One advantage to the placement of the stimulation lead in this method is that the stimulation lead denervates a mesh of nerves that are well confined in a relatively tight space and therefore, a more predictable location is selected for treatment of the SI joint. It is also contemplated within this method that additional nerve branches can be denervated, such as the nerve branches extending from the lumbar segments. Another advantage in this method is that since the lesion is confined within the defined enclosed space, it is possible to generate a large cylindrical lesion that would entirely fill the space, thereby ensuring adequate lesioning of all of the nerve tissue within the enclosed space. Further, because the lesion is guarded by the sacrum, injury to the skin, even in a small patient, is very unlikely. Additionally, the tissues in this confined location are most exclusively ligamentous, and thus a much more consistent lesion can be made since the resistive characteristics of the tissue are constant throughout the area contacted. In comparing the location of the stimulation lead 624 in FIG. 58 as compared to the location of the stimulation lead in FIG. 23, it is clearly noted that the stimulation lead is placed more laterally to lie captured under the iliac crest, in contact with the sacrum, and either on or immediately medial to the dorsal SI joint.

Figure 59:
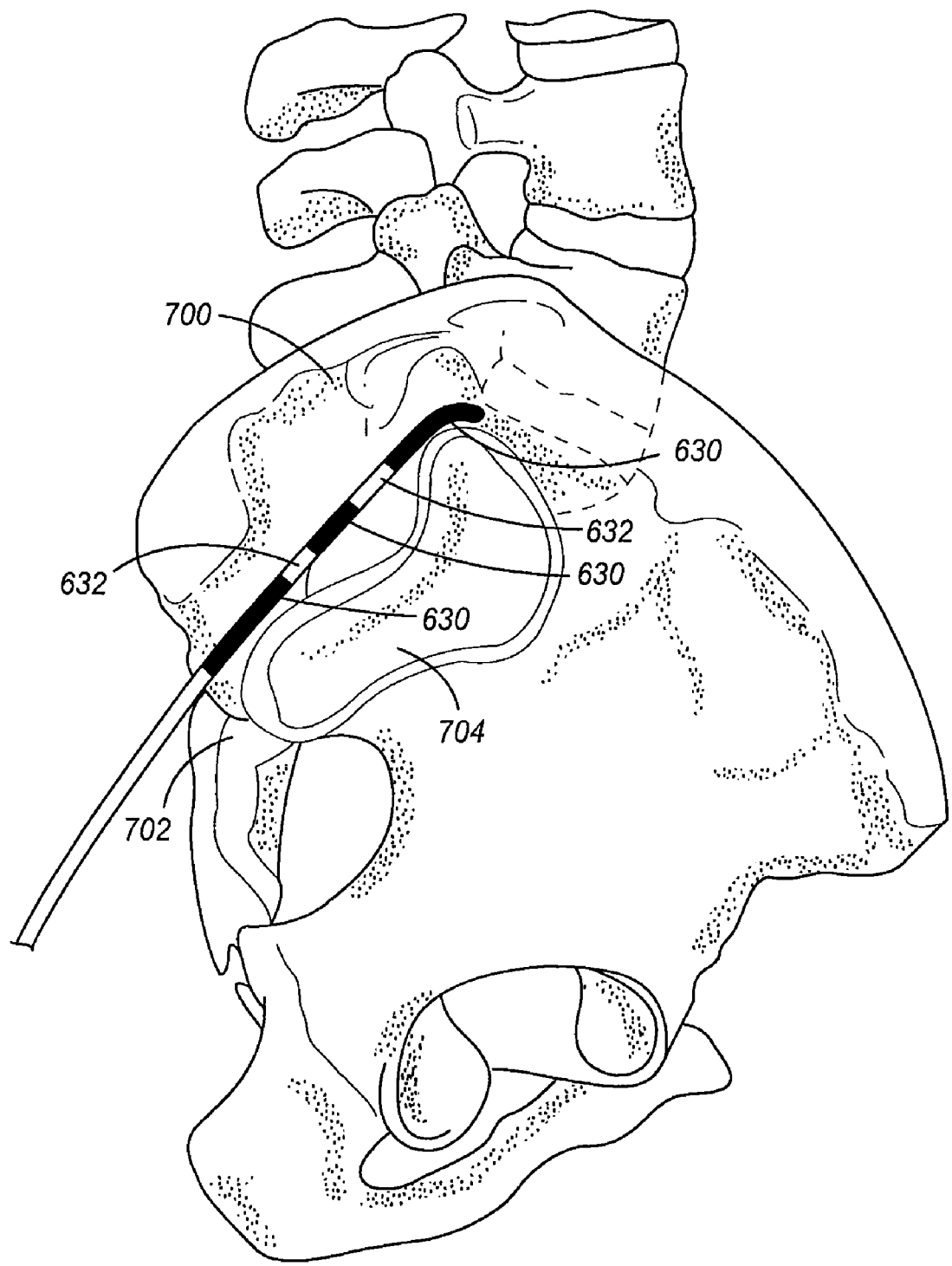
FIG. 59 is a lateral/side-view of the sacral region showing placement of the stimulation lead of FIG. 56 wherein the stimulation lead lies in the enclosed space confined between the iliac crest/ilium above, the SI joint laterally, and the sacrum below.
Figure 60:
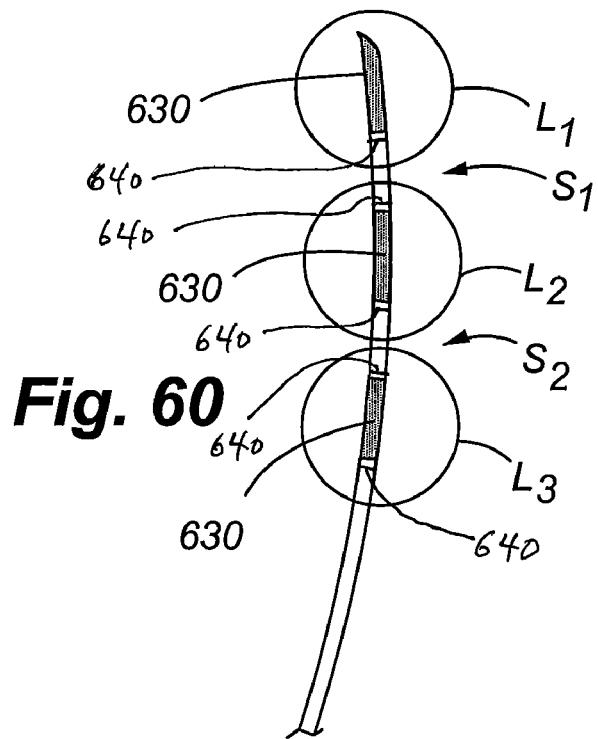
FIG. 60 is schematic view of a lesion pattern that is achieved by mono-polar activation of the stimulation leads of the stimulation device of FIG. 56.

As shown in the lateral view of FIG. 59, this figure also shows placement of the stimulation lead 624 where it lies captured under the iliac crest 700, in contact with the sacrum 702 and on or immediately medial to the SI joint 704. Although FIG. 59 is only a two-dimensional representation of placement of the stimulation lead with respect to the sacroiliac region, those skilled in the art can understand how from the foregoing description along with the figures that the stimulation lead is placed within the defined confined space to achieve creation of an ablative area which can effectively render the surrounding nerve tissue non-functional Now referring to FIGS. 60 and 61, in accordance with the method of FIG. 58, it is also contemplated that a cylindrically shaped lesion can be effectively created by selecting a particular sequence and mode of lesioning through activation of selected electrodes on the stimulation lead. Referring first to FIG. 60, it is shown that there are three active areas or electrodes 630 on the stimulation lead. Mono-polar activation of the respective electrodes results in generally circular or curved shaped lesions created, shown as lesions $L_1$, $L_2$, and $L_3$. In a three dimensional aspect the lesions $L_1$, $L_2$, and $L_3$ are generally formed in a spherical shape where there may be definable gaps or spaces between the lesions, annotated as spaces $S_1$ and $S_2$. If the electrodes 630 are positioned closer to one another, then it may be possible to reduce the gaps or spaces between the individual lesions; however, because of power constraints with RF medical devices, it is difficult to generate a lesion large enough to treat the entire targeted SI joint without having to conduct a series of activations and by then moving the stimulation lead to a next location and then energizing the electrodes again. Therefore, at least with respect to treatment of the SI joint, it is not feasible to simply provide one long electrode that can generate enough energy to ablate the surrounding tissue. In accordance with the method of the present invention, in order to create a substantially uniform, cylindrical shaped lesion that is large enough to treat the targeted area, after mono-polar activation of the electrodes forming lesions $L_1$, $L_2$, and $L_3$, the mode of operation of the stimulation lead is changed such that the spaces $S_1$ and $S_2$ can be filled in by lesions $L_4$ and $L_5$. Lesion $L_4$ may be created by a bipolar activation of the most distal electrode and the middle electrode. Creation of lesion $L_5$ may be created by a bipolar activation of the middle and proximal electrodes. Thus, the sequence of activation would be mono-polar activation of the electrodes to create lesions $L_1$, $L_2$, and $L_3$, followed by bipolar activation of the distal and middle electrodes, and bipolar activation of the middle and proximal electrodes to form lesions $L_4$ and $L_5$. In accordance with functionality adopted within the RF generator 614, a sequence of software commands could allow the user to manipulate not only the length of time and power applied to the electrodes, but also the specific sequence to include the bifurcated mono-polar and bipolar activations.

Figure 61:
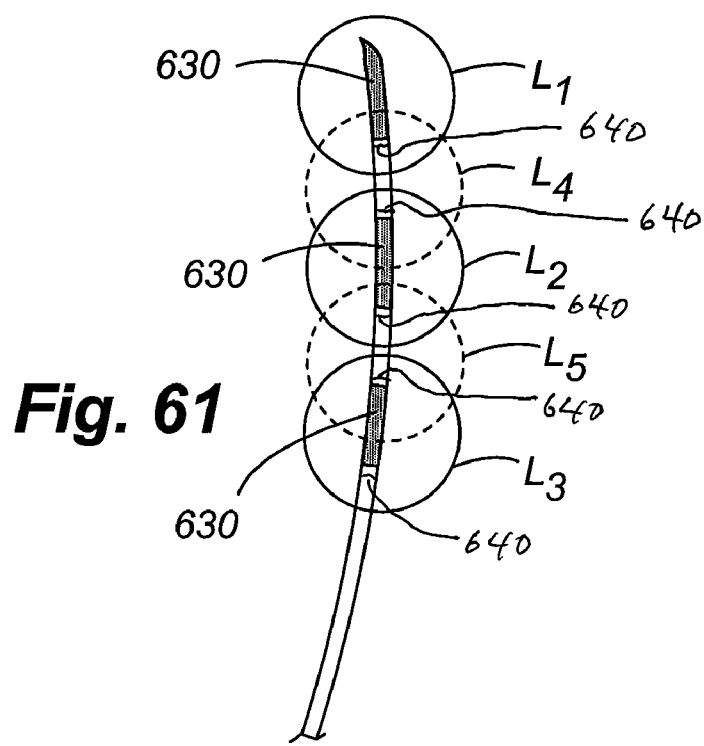
FIG. 61 is a schematic representation of the lesion that is created by supplementing the mono-polar activation of the stimulation leads by bipolar activation of the stimulation leads wherein gaps in the lesion of FIG. 59 are filled in to create a more uniform, strip-like lesion pattern.

FIGS. 60 and 61 also illustrate radio opaque markers 640 that can be used to better visualize the exact location of the electrodes 630 during a procedure. Electrodes may be typically made from stainless steel. Electrodes made of stainless steel are very difficult to see, for example, when using fluoroscopy during the procedure being conducted. Thus, it is difficult for the practitioner to know the exact location of the electrodes, which therefore negatively affects the ability to precisely locate the ablative pattern to be created. The radio opaque markers 640 may be small bands made of radio opaque materials, such as platinum or iridium. These bands as shown can be located at the proximal and distal ends of the electrodes such that when a practitioner visualizes the placement of the device during a procedure, the markers 640 clearly delineate the locations of the electrodes and therefore allowing precise placement of the device to create the desire ablative pattern. Although not shown, the most distal electrode could also have a distal marker however it would be understood that the proximal marker for the most distal electrode would suffice for locating that electrode in an image being viewed.

One clear advantage with respect to the device shown in FIG. 56 and the method described with respect to FIGS. 60 and 61 is that treatment of the SI joint may be achieved by a single element wherein the probe does not require the use of an introducer needle, stylet, or any other guidance device. Furthermore, complete denervation may be achieved by a single placement of the stimulation lead at the location shown in FIGS. 58 and 59. Thus, after the sequence of electrode activations has occurred, an adequately sized lesion is generated to treat the SI joint and the stimulation lead does not have to be repeatedly repositioned or reinserted into the patient for further lesioning. The unique handle design maximizes push and twist maneuverability for the user such that the stimulation leads may be placed in the desired area within the sacral region.

Another example medical procedure that may be conducted with one or more of the stimulation leads of the present invention includes treatment of the superior hypogastric plexis. For this procedure, the patient will be placed in a prone position. The vertebral body end plates of L5 and S1 would be brought into alignment with a fluoroscopy beam. An introducer needle is inserted lateral to the superior articulur process of S1 and infero-medial to the L5 nerve root and placed alongside or partially through the annulus of the L5-S1 intervertebral disc so that the curved tip is positioned at the inferior ventro-lateral aspect of the L5-S1 disc as viewed on a lateral projection. A stimulation lead of the present invention is then inserted through the introducer needle and directed to lie at or slightly cephalad to the sacral prominons in the prevertebral space and extending across the width of the vertebral body as viewed on an AP projection. If the lead cannot be positioned all the way across the width as described, a bilateral approach can be employed. Myelogram safe contrast medium may be infused through the infusion ports of the lead to ensure appropriate tissue plane placement and away from unintended neural, vascular, or other soft tissue structures. Local anesthetic is then injected through the lead and a lesion or stimulation is carried out using determined protocols and activating the contacts necessary to achieve optimum therapy.

For each of the embodiments, it is also contemplated that the devices may be constructed of materials that are compatible with the imaging technique used to visualize the procedure being conducted. For X-ray and CT scanning techniques, standard materials are typically imaged in an acceptable fashion however if it is desired to use magnetic resonance imaging (MRI), special consideration may be required in selection of materials so that the device does not create a large image artifact. Two examples of acceptable materials that may be used as MRI compatible include non-magnetic alloys of stainless steel and titanium.

For each embodiment discussed above, it should also be understood that each of the active electrical conductive areas or electrodes may be independently connected to a source of power such that each of the electrodes may be selectively energized or de-energized to provide the desired ablative pattern or electrical field. It is also desirable to provide a temperature-sensing element at each of the electrode locations, such as the illustrated thermocouples. Although thermocouples are shown, it shall be understood that other temperature elements may be used to sense or otherwise measure temperature such as RTDs, and others. With respect to control of each of the active electrical areas, it shall be understood that a controller can be used to measure temperature/energy applied at each of the conductive locations, as well as providing a visual indication as to how much energy has been applied over a period of time.

With respect to the distal tips of each of the different stimulation leads and disposable sheaths, it shall be understood that the distal tips may be active, electrical areas/electrodes. Thus, in addition to electrodes being selectively spaced along the length of the stimulation lead, the distal tips may also provide electrical or thermal energy to targeted tissue.

Based upon the foregoing, the present invention provides a combination electrical and chemical stimulation lead especially adapted for treatment of many types of ailments to include, disc ailments SI joint ailments, and other spine ailments to include treatment of structures that have large and diffuse innervations such as, but not limited to, the superior hypogastric plexus, sympathetic chain, ganglion impar, zygapophyseal joints, and others.

The various embodiments provide a treating physician with stimulation leads of various configurations, which optimizes a physician's ability to precisely position the stimulation lead, as well as to precisely direct both electrical and chemical stimulation.

While the above description and drawings disclose and illustrate embodiments of the present invention, it should be understood that the invention is not limited to these embodiments. Those skilled in the art may make other modifications and changes employing the principles of the present invention, particularly considering the foregoing teachings. Therefore, by the appended claims, the applicant intends to cover such modifications and other embodiments.

What is claimed is:

1. A method of managing SI joint pain in a sacrum of a patient, said method comprising the steps of:
  providing a stimulation lead having (i) a body with a curve extending along a length thereof, and said stimulation lead having a distal end with a bend incorporated thereon to assist in steering said stimulation lead and (ii) a plurality of electrodes positioned on said stimulation lead, said electrodes communicating with a source of electrical energy;
  inserting the stimulation lead into a patient in a position to lie captured under an ilium of the patient and in contact with a sacrum of the patient, on or directly medial to a dorsal SI joint of the patient; and
  activating said plurality of electrodes to denervate tissue surrounding the stimulation lead, including lateral branches of nerves within a defined enclosed space between the ilium and sacrum and spaced from an origin of the lateral branches.

2. A method, as claimed in claim 1, further including the step of:
  infusing through said stimulation lead at least one chemical selected from the group consisting of an anesthetic, a neurolytic, a proliferant, and a nutrient.

3. A method, as claimed in claim 1, wherein:
  said plurality of electrodes are spaced along a length of said stimulation lead.

* * * * *